United States Patent [19]
Demarest et al.

[11] Patent Number: 6,115,650
[45] Date of Patent: Sep. 5, 2000

[54] ROBOTIC CONTROL SYSTEM FOR NEEDLE SORTING AND FEEDER APPARATUS

[75] Inventors: David D. Demarest, Parsippany; Teresa Shaw, Plainsboro, both of N.J.

[73] Assignee: Ethicon, Inc., Somerville, N.J.

[21] Appl. No.: 09/016,455

[22] Filed: Jan. 30, 1998

Related U.S. Application Data

[63] Continuation-in-part of application No. 08/848,927, Apr. 30, 1997, Pat. No. 6,012,216.

[51] Int. Cl.[7] .................................................. G05B 15/00
[52] U.S. Cl. .............................. 700/259; 700/245; 901/7
[58] Field of Search ...................................... 700/245, 247, 700/259, 59, 62, 56, 112–114, 213, 230; 382/153; 901/7, 9, 47; 163/5; 414/754, 758, 783

[56] References Cited

U.S. PATENT DOCUMENTS

| | | | |
|---|---|---|---|
| 2,736,194 | 2/1956 | Dilts | 73/88 |
| 3,857,313 | 12/1974 | Endo | 83/277 |
| 4,011,155 | 3/1977 | Feurstein et al. | 209/74 R |
| 4,187,051 | 2/1980 | Kirsch et al. | 414/744 |
| 4,358,976 | 11/1982 | Alviti | 83/66 |
| 4,412,293 | 10/1983 | Kelley et al. | 364/513 |
| 4,437,114 | 3/1984 | LaRussa | 358/101 |
| 4,475,404 | 10/1984 | Rutledge, Jr. et al. | 73/827 |
| 4,672,871 | 6/1987 | Gudmestad | 83/151 |
| 4,744,035 | 5/1988 | Hashim | 364/470 |
| 4,806,737 | 2/1989 | Coates | 219/390 |
| 4,835,450 | 5/1989 | Suzuki | 318/568.13 |
| 4,909,376 | 3/1990 | Herndon et al. | 198/395 |
| 4,942,796 | 7/1990 | Dom et al. | 83/72 |
| 5,065,237 | 11/1991 | Tsikos et al. | 358/101 |
| 5,131,533 | 7/1992 | Alpern | 206/63.3 |
| 5,150,307 | 9/1992 | McCourt et al. | 364/478 |
| 5,156,788 | 10/1992 | Chesterfield et al. | 264/157 |
| 5,195,234 | 3/1993 | Pine et al. | 29/720 |
| 5,370,216 | 12/1994 | Tsuruyama et al. | 198/395 |
| 5,438,746 | 8/1995 | Demarest et al. | 29/564.6 |
| 5,473,810 | 12/1995 | Demarest et al. | 29/712 |
| 5,568,593 | 10/1996 | Demarest et al. | 700/247 |
| 5,660,024 | 8/1997 | Ivanov et al. | 53/430 |
| 5,661,954 | 9/1997 | Ivanov et al. | 53/430 |

FOREIGN PATENT DOCUMENTS

| | | |
|---|---|---|
| 63-299834 | 12/1988 | Japan . |
| 2 167 211 | 5/1986 | United Kingdom . |
| 92/03364 | 3/1992 | WIPO . |

*Primary Examiner*—William Grant
*Assistant Examiner*—Steven R. Garland
*Attorney, Agent, or Firm*—Scully, Scott, Murphy & Presser

[57] ABSTRACT

A control system for a needle singulation and infeed apparatus that automatically picks up surgical needles in random, un-oriented positions on a transport conveyor or like device, and places them in oriented positions for suture attachment at a fully automated needle swaging station. The apparatus employs one or more robot devices for picking up the needles and placing them in individual precision engagement devices for sequential conveyance to an automatic swaging machine. After gripping the needle, and, depending upon the orientation of the needle with respect to the robot gripper, the robot gripper can pick the needle and move to a location where a mechanical finger is fixedly positioned. The robot is programmed to move to the mechanical finger and tap the needle held by the robot gripper against the finger to orient or rotate the needle in the proper direction prior to placing the needle in the precision engagement device. This, obviates the need for a further needle orienting step downstream of the robot pick and place location and ensures the high-speed transport of highly oriented needles for the automatic swaging operation.

32 Claims, 21 Drawing Sheets

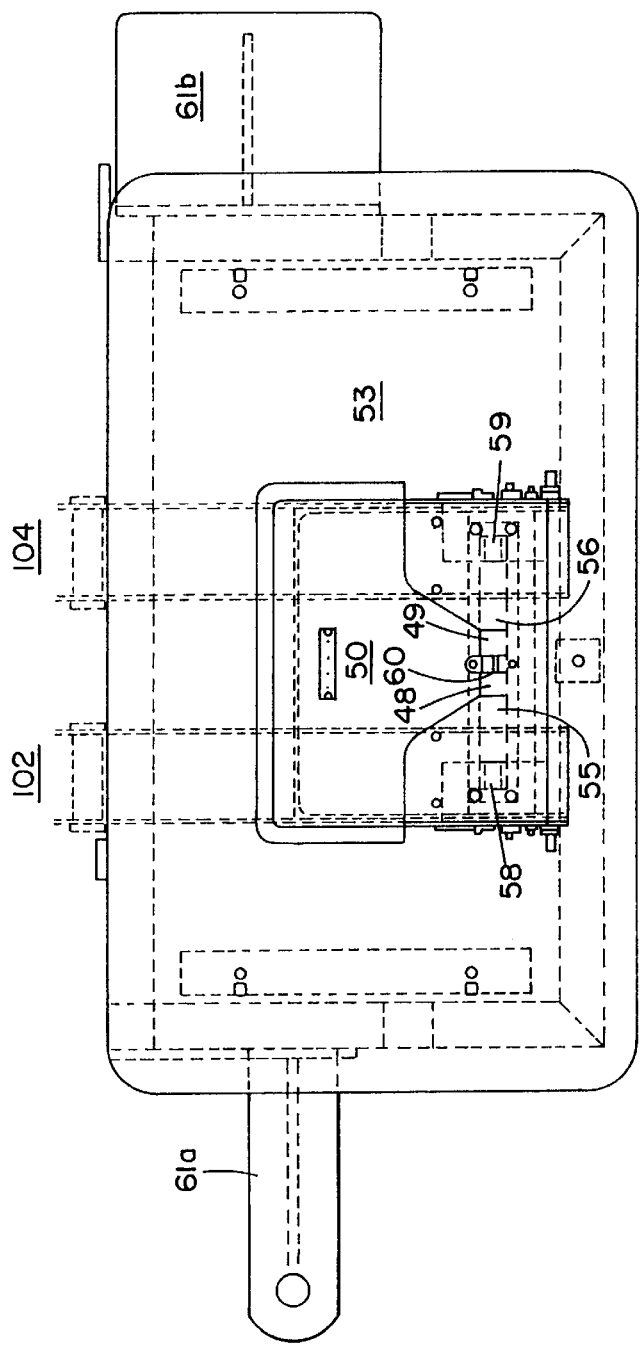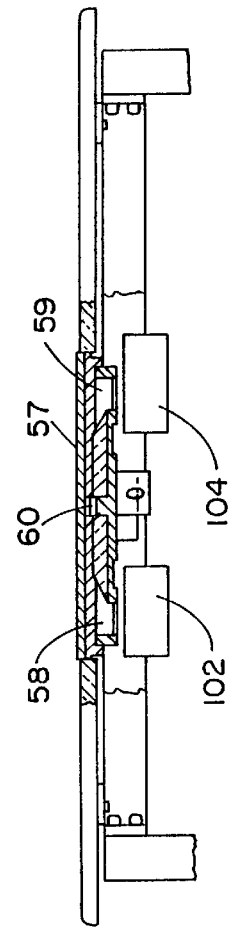
FIG.7(a)
FIG.7(b)

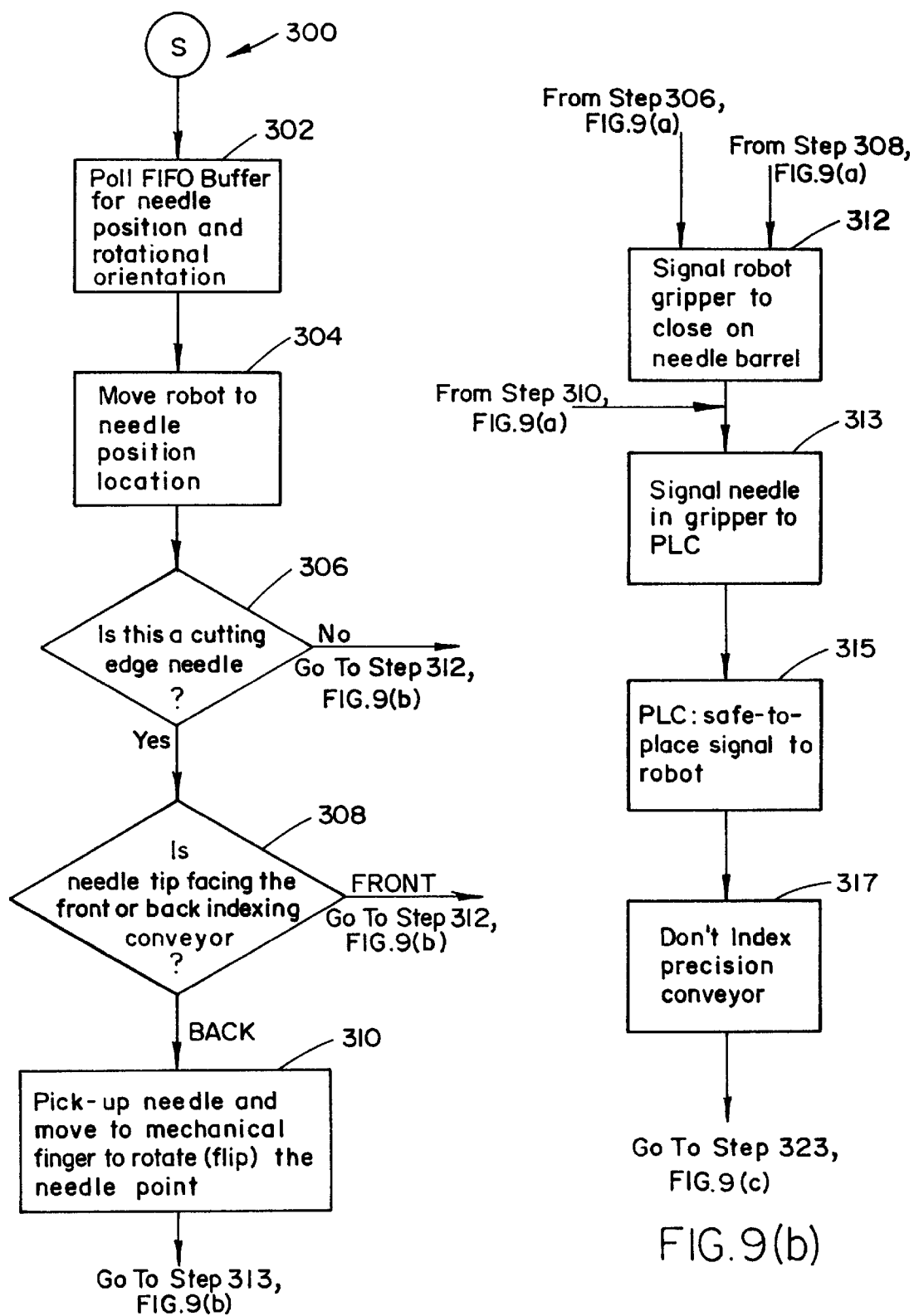

ROBOTIC CONTROL SYSTEM FOR NEEDLE SORTING AND FEEDER APPARATUS

This patent application is a continuation-in-part patent application of patent application Ser. No. 08/848,927, now U.S. Pat. No. 6,012,216, for STAND ALONE SWAGE METHOD AND APPARATUS, filed Apr. 30, 1997.

FIELD OF THE INVENTION

The present invention relates generally to machines for automatically swaging needles, such as surgical needles to a suture, and more specifically, to a control apparatus for singulating unsorted needles and orienting them for subsequent automatic swaging to a suture.

DESCRIPTION OF THE PRIOR ART

This application describes improvements to a control system for an automatic needle and suture swaging apparatus disclosed in a series of U.S. Patents, of which U.S. Pat. No. 5,438,746 entitled "Needle Threading and Swaging System"; and U.S. Pat. No. 5,568,593 entitled "Robotic Control System for a Needle Sorting and Feeding Apparatus" are typical. All of these patents are assigned to the assignee of the present invention, and are hereby incorporated by reference herein.

The automatic needle and suture swaging machine described in the above referenced U.S. Patents is a highly automated machine intended for high volume production and packaging of armed needles, i.e., needles and sutures wherein 20,000 to 40,000 needles and sutures are to be produced in a single run, needles with attached sutures. As illustrated in FIG. 2, the surgical needle 39 includes a ground or cutting edge portion 40 and is illustrated with an attached suture 42 which has been attached by swaging as indicated at 44. The suture 42 may be of any predefined length, but is commonly provided in lengths that are multiples of nine inches (18, 27 and 36 inch suture sizes are particularly common).

The Robotic Control System for a Needle Sorting and Feeding Apparatus described in the above-referenced U.S. Pat. No. 5,568,593 describes a system for sorting and singulating needles and precisely orienting them in an manner sufficient to automatically perform a needle-suture swaging operation. Particularly, in the prior art needle sorting process 10 shown in FIG. 1, needles are first loaded into one or more vibratory bowls at step 11, automatically sorted and linearly fed at step 12 to each of two translucent indexing conveyors at step 13, evaluated with respect to orientation and position by a vision tracking system at step 14, picked up by a robot gripping apparatus comprising first and second robots at step 15, transferred to a engagement boat of a precision conveyor by the robot apparatus at step 16, and finally transferred in an oriented position to a multiaxis gripper means for further conveyance to a subsequent swaging workstation at step 17.

Particularly, the robotic control system described in the above-referenced U.S. Pat. No. 5,568,593 comprises various robot control, vision control and conveyor indexing control tasks enabling un-oriented surgical needles to be processed and fed to a swaging station in a precisely oriented position to an accuracy to within approximately 0.001 inches as required for automatic swaging.

It has been determined that certain surgical needles having super-sharp cutting edges can become blunted while being sorted and singulated in the vibratory bowls described in the aforementioned patent. Additionally, such super sharp surgical needles appear to the vision tracking system as arcs having similarly shaped barrel (suture receiving) end and cutting ends. Thus, it is vitally important that the vision system detect which is the barrel end and which end is the cutting end so that the robot pick and place operation may be performed correctly. Otherwise, the subsequent swage operation will fail.

Prior art techniques essentially require a pixel count comparison whereby, after locating the end points of an acceptable needle, a predetermined boxed area is formed around each of the endpoints and a pixel count comparison is initiated for determining the amount of needle thickness at each end point. For the majority of needles contemplated, the barrel end is larger than the point end, so that a pixel count could easily differentiate the point end from the barrel. However, the super sharp cutting-edge needles have a flared tip, which may be wider than at the barrel end, thus rendering any pixel amount comparison technique inaccurate.

SUMMARY OF THE INVENTION

The invention is directed to an improved semi-automatic needle singulation and infeed apparatus that inputs super-sharp cutting edge surgical needles to an automatic swage dial assembly for the swaging of needles to sutures fed and cut to length by the apparatus.

It is an object of the present invention to provide a control system for a needle infeed apparatus machine which will efficiently handle small batches or production runs on needles and to efficiently handle premium needles and super sharp cutting edge needles in an efficient manner without blunting the cutting edge of the needle.

It is another object of the present invention to provide a needle singulating apparatus for assisting an operator in singulating cutting edge surgical needles for subsequent swaging in an automatic swaging machine, wherein the apparatus includes a needle sliding surface, a pair of drop openings for receiving the singulated needles, and means to position the singulated needles in a spaced apart relationship on a transport conveyor for transport to a precise positioning apparatus. The precise positioning apparatus then positions the needle at a first predetermined position for hand-off to an automatic swaging apparatus.

Particularly, the present application is directed to a control system for a needle singulation and infeed apparatus that automatically picks up surgical needles in random, un-oriented positions on a transport conveyor or like device, and places them in oriented positions for suture attachment at a fully automated needle swaging station. The apparatus employs a camera assembly for obtaining pixel images of the needles and one or more robot devices for picking up the needles and placing them in individual precision engagement devices for sequential conveyance to an automatic swaging machine. Depending upon the orientation of the needle on the transport conveyor, the robot gripper can be instructed to move to a location where a mechanical finger is positioned so that the surgical needle may contact the finger and properly orient or rotate the needle while being gripped before placing the needle in the precision engagement device. This step obviates the need for a further needle orienting step downstream of the robot pick and place location, e.g., by a plow, thus ensuring minimal contact of the needle with mechanical devices during transport all the while maintaining high-speed transport of highly oriented needles for the automatic swaging operation.

To differentiate the needle point from barrel end, an improved algorithm for processing the imaged data is implemented whereby, the taper of the needle at each end point is determined. A comparison of the taper ratios, i.e., change in thicknesses, at each end point will determine which end is barrel and which end is the cutting edge.

BRIEF DESCRIPTION OF THE DRAWINGS

FIG. 7(a) is a top plan view of the needle singulating station of the present invention.

FIG. 7(b) is a partially cross-sectioned elevation view of a portion of the needle singulating station illustrated in FIG. 7(a).

FIGS. 9(a)–9(g) illustrate the flow diagrams for the various robot control, vision control, and conveyor indexing tasks to be performed by the needle infeed control system of the instant invention.

DETAILED DESCRIPTION OF THE PREFERRED EMBODIMENT

The present invention is directed to a control system for a needle infeed apparatus that is designed to automatically, or, preferably, semi-automatically sort, singulate, and convey surgical needles of various sizes to an automatic swaging station where sutures are attached to individual needles. Preferably, the control system is implemented in an improved stand alone swage machine that is particularly adapted to assist in the semi-automated singulation of surgical needles to enable subsequent automated handling of the needle, automatic swaging, automatic pull-testing of the armed needle, and future packaging. Details of the stand alone swage machine can be found in co-pending U.S. patent application No. 08/847,133, now U.S. Pat. No. 5,911, 449, and U.S. patent application No. 08/848,927, now U.S. Pat. No. 6,012,216, assigned to the same assignee of the present invention and the contents and disclosures of which are incorporated by reference herein.

Additionally, the invention particularly incorporates various improvements to the robot control and vision control tasks as disclosed in U.S. Pat. No. 5,568,593 entitled "Robotic Control System for a Needle Sorting and Feeding Apparatus," assigned to the assignee of the present invention, which tasks provide for the recognition (location) of un-oriented surgical needles, i.e., the vision task, and, provides for coordinated robotic movement for gripping and transferring of the un-oriented surgical needles to an engagement boat of a precision indexing conveyor, i.e., the robot control task.

Figure 1A:
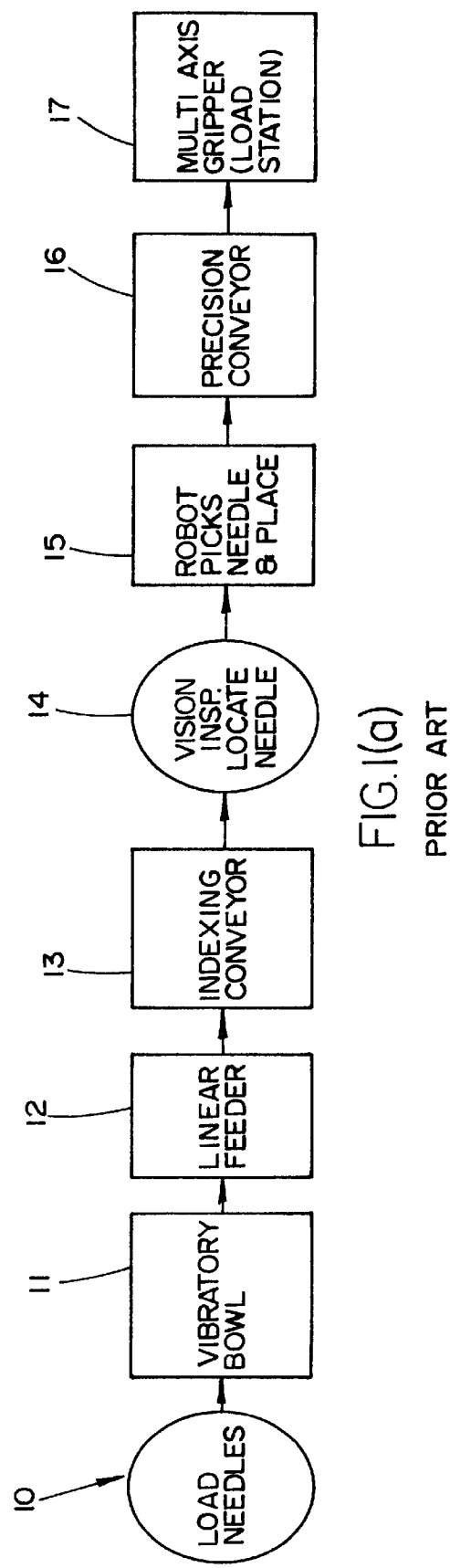
FIG. 1(a) is a block diagram showing the process flow for the needle sorting apparatus of the prior art.
Figure 1B:
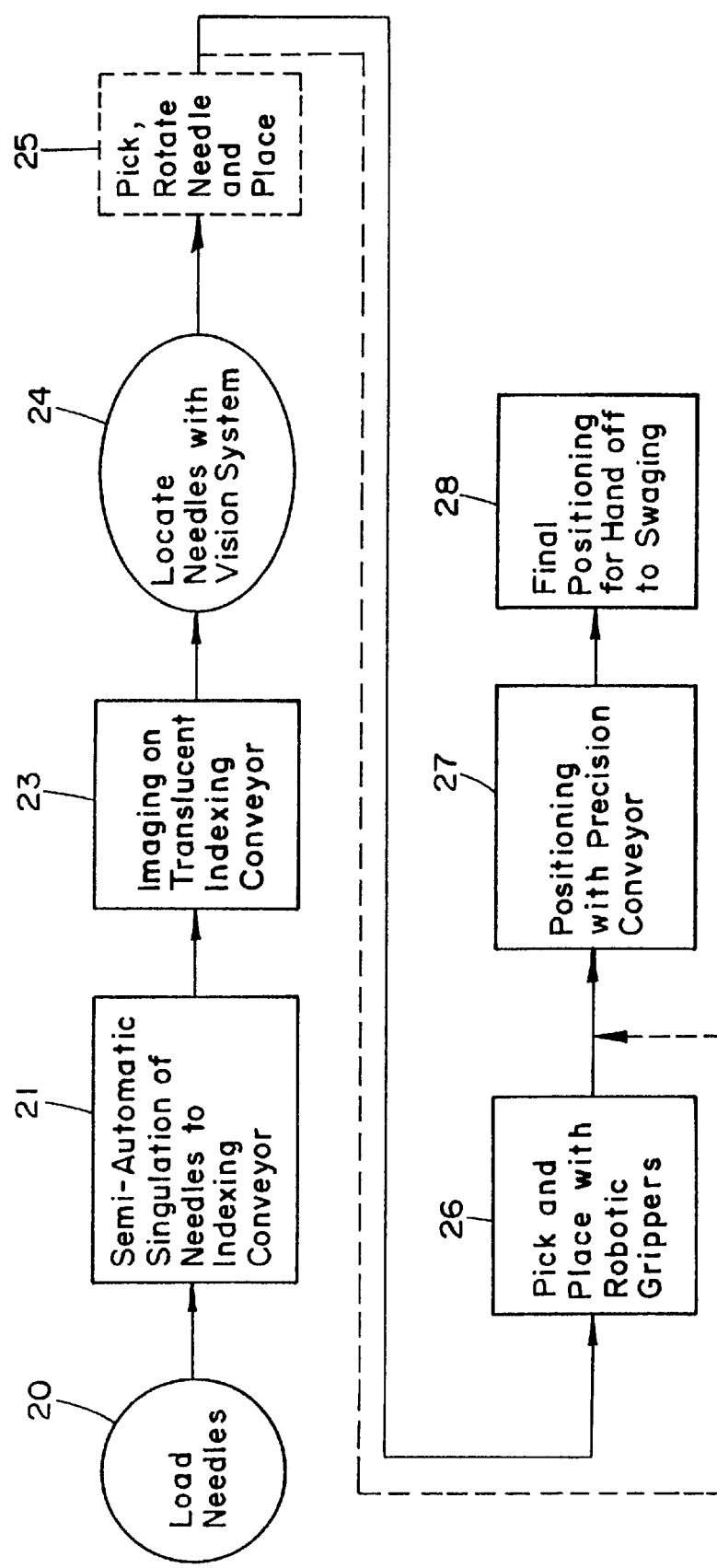
FIG. 1(b) is a block diagram showing the process flow for the needle sorting apparatus of the present invention.
Figure 2:
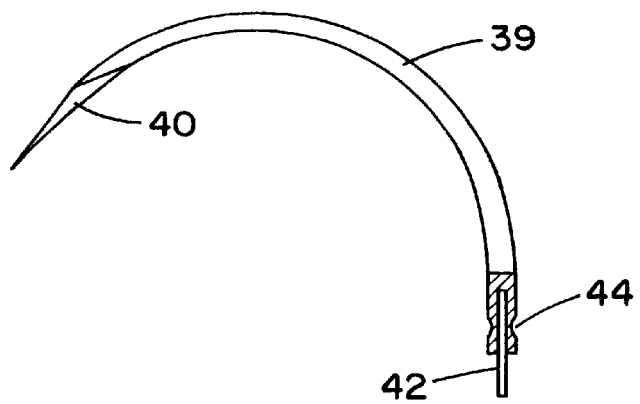
FIG. 2 is a surgical needle 19 with showing super-sharp edge and barrel portion having an attached suture crimped thereto.

In the preferred semi-automated needle sorting process 20 shown in FIG. 1(b), super-sharp cutting edge needles are manually singulated by operators at step 21 who sort and linearly feed the needles onto a translucent indexing conveyor at step 23. The needles are evaluated with respect to orientation and position by a vision tracking system at step 24, picked up by one or more robot devices at step 26, and transferred to an engagement boat of a precision conveyor by the robot device at step 27, and finally conveyed to a multiaxis gripper means mounted on an indexing swage dial for further conveyance to subsequent swaging workstation at step 28. The particular improvements occurs at step 24 where the vision control task employs algorithms for determining the orientation of the needle with respect to the location of the robot gripper, and, an optional step 25, where, depending upon the needle's orientation, a robotic control command may be generated to pick the needle and move to a location provided with a mechanical finger adapted to "flip" the needle, i.e., rotate its orientation by 180°, prior to placing the needle on a conveyor boat. As will be described this flipping of the needle will enable precise handling and transference of the needle from the precision engagement boat to the subsequent swaging station. Additionally, in this manner, further physical contact with the super-sharp cutting edge of the surgical needle is minimized.

Figure 4A:
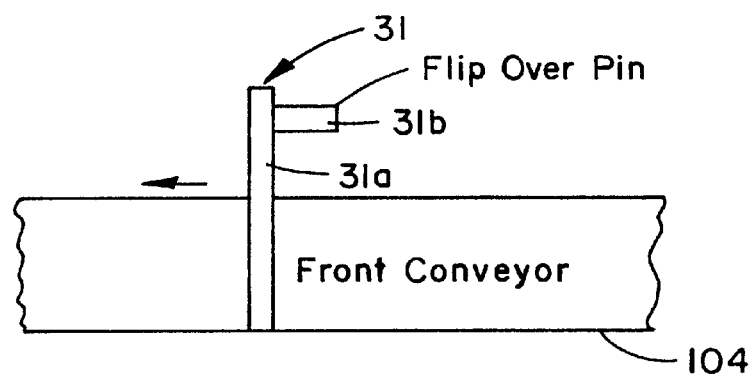
FIG. 4(a) illustrates an elevational view of a portion of the apparatus shown in FIG. 4 showing the flip-over bar.
Figure 4B:
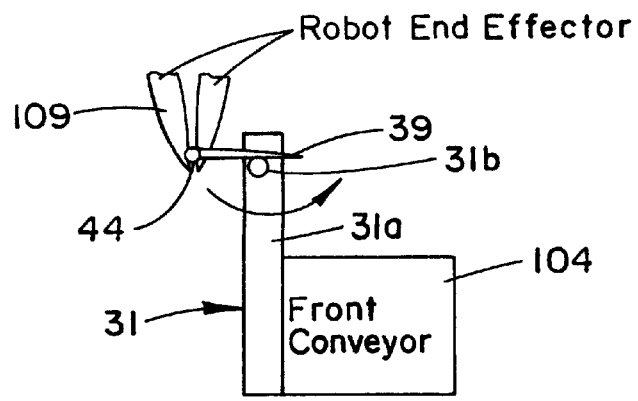
FIG. 4(b) illustrates a front view showing a needle orientation being rotated while in the robot gripper.
Figure 3:
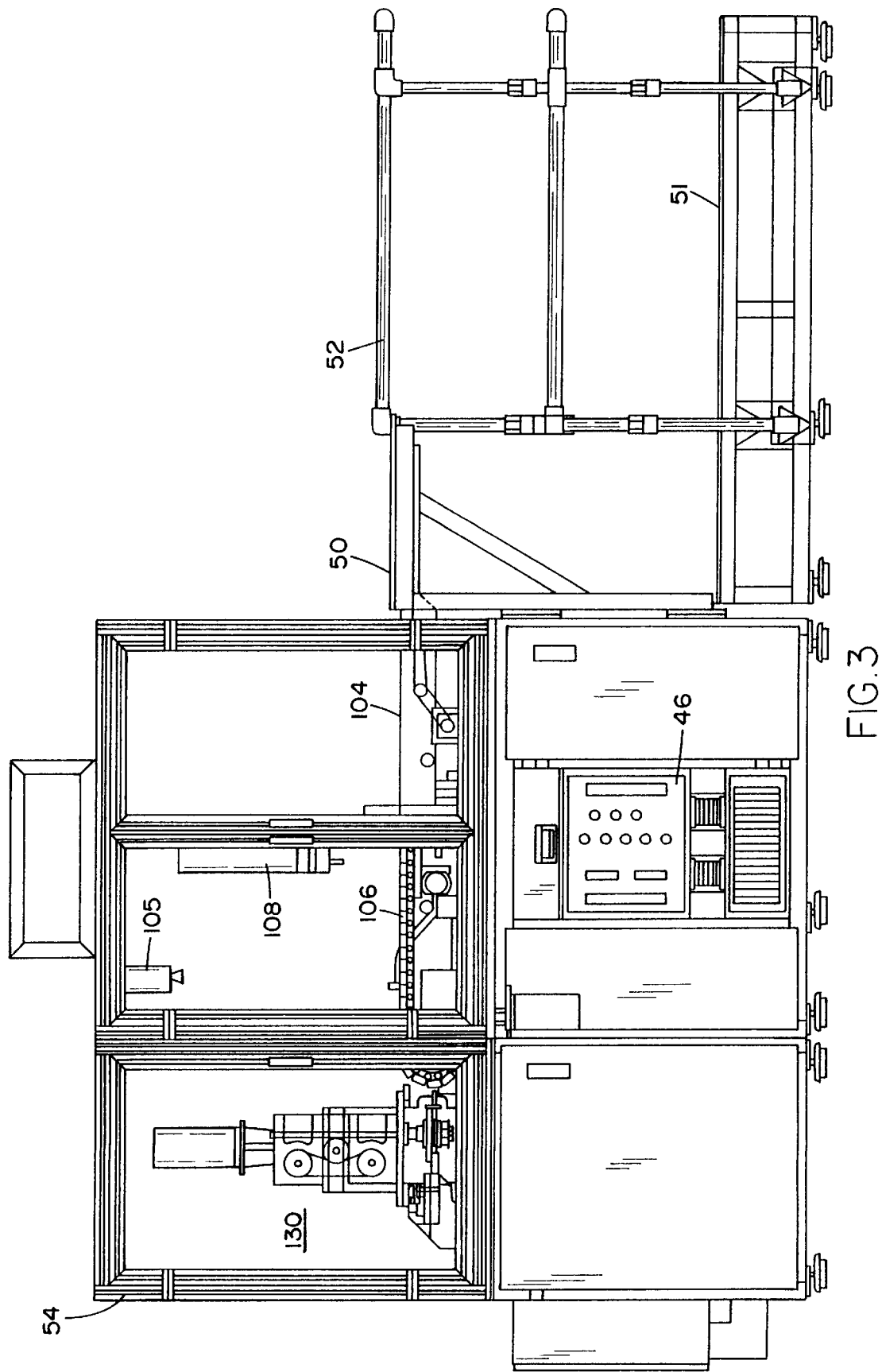
FIG. 3 is a side elevational view of the needle sorting device illustrating an operator station, a control computer, portions of the automatic swage machine and portions of the robotic handling device, including the robot assembly and vision tracking devices.
Figure 4:
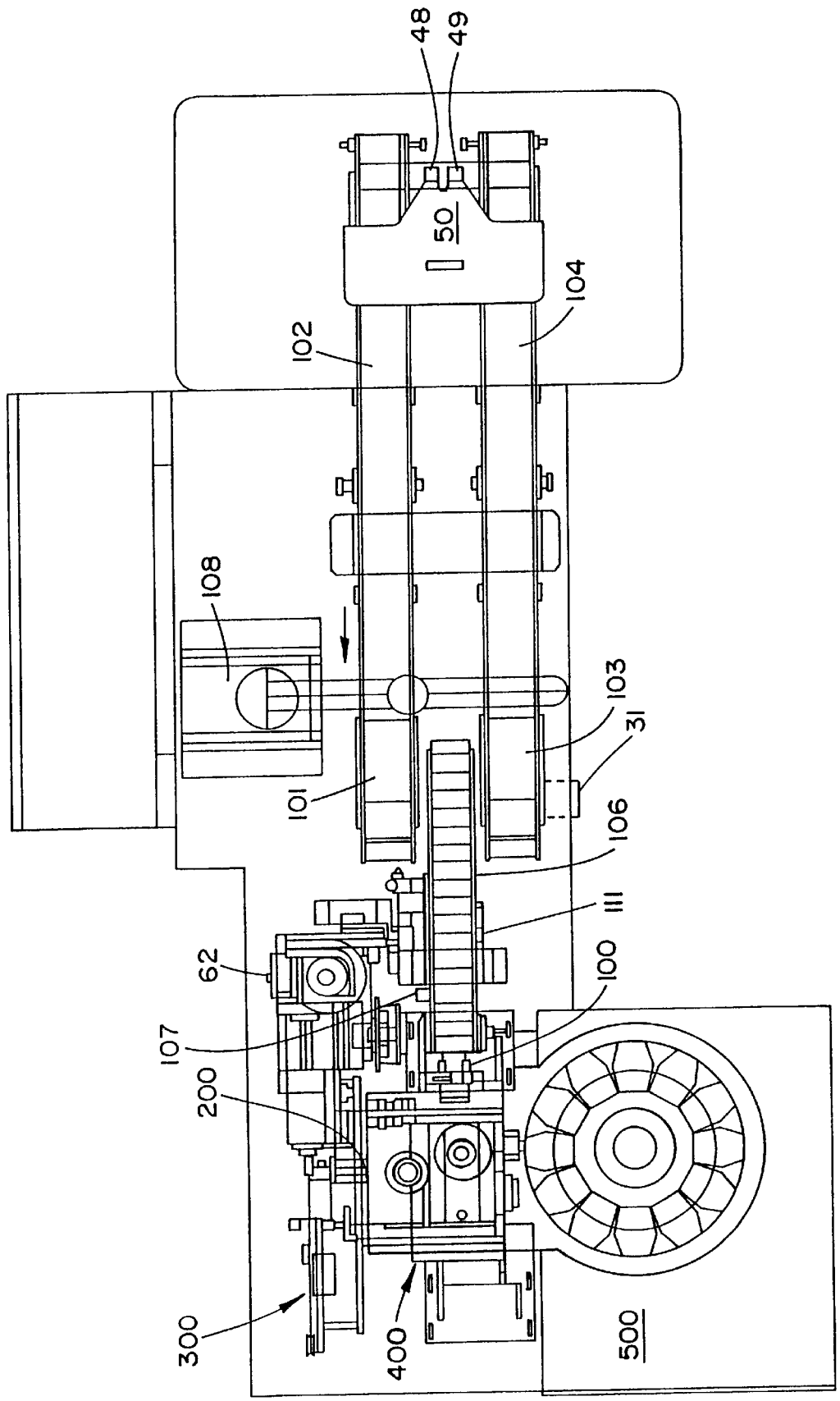
FIG. 4 is a top plan view of the needle sorting apparatus controlled by the robotic control system of the present invention.
Figure 5:
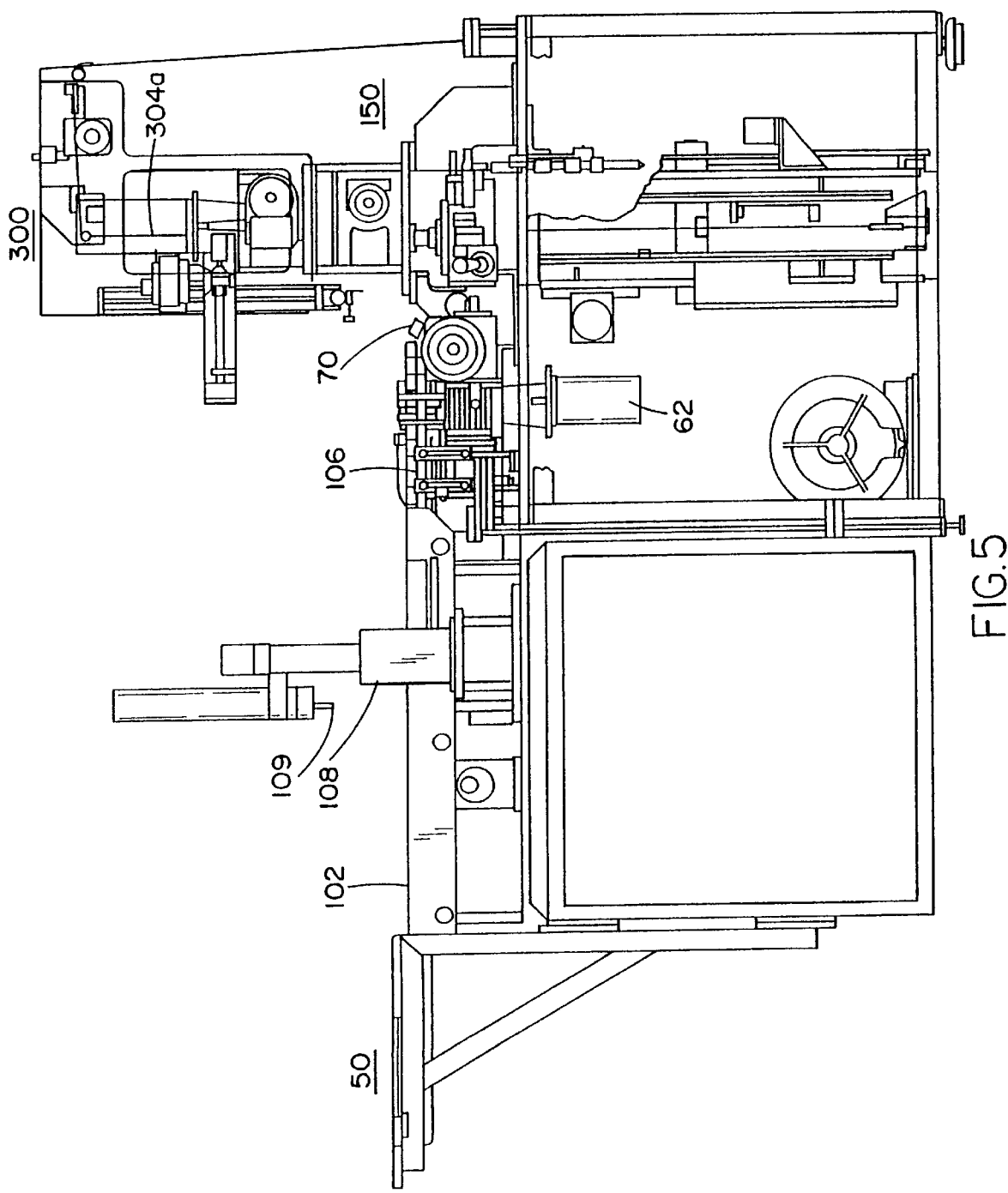
FIG. 5 is a detailed elevation side view of the present invention from the opposite side as illustrated in FIG. 3, with the operator safety guards removed.

FIG. 3 is an elevation view of one side of an apparatus implementing the robotic control system of the present invention, and FIG. 4 is a top plan view of the needle-infeed and automatic swaging and apparatus with the safety guards removed. FIG. 5 illustrates the apparatus from the opposite side as FIG. 3. FIGS. 3–5 are used in the following descriptive overview of the apparatus. This apparatus includes a singulation surface 50 on table 53 to assist an operator in singulating needles that are deposited to the translucent conveyors 102,104, one of the conveyors 104, being depicted in FIG. 3. The operator work station includes a platform 51 for operator seating and guard rails 52 for operator safety. Safety guards 54 are also provided around the machine for safety purposes.

Each of the needles singulated by the operator are dropped through openings 48,49 by sliding the needle along the singulation surface 50. This step avoids the needle to needle contact inherent in the vibratory feed bowls illustrated in U.S. Pat. No. 5,473,810 and thus substantially reduces the risk that premium needles or cutting edge needles will be blunted by needle contact. As each needle is dropped, it lands at an intermediate staging location, and at an appropriate interval, after each index of the indexing conveyor, the needles are blown by a puff of air to the translucent indexing conveyor, with needles dropped through opening 48 being transferred to translucent indexing conveyor 102 and needles being dropped through opening 49 being transferred to translucent indexing conveyor 104.

The needles thus transferred are indexed forward to imaging stations 101,103 wherein a back light provides a high contrast image of the needle against a white background for imaging purposes. The indexing conveyors 102, 104 are indexed approximately 2 inches at each index. By limiting the incremental advancement the image processing is step is enhanced, and problems associated with inertial loads on the needles on conveyors 102,104 are minimized. If the indexing conveyors 102,104 are accelerated too quickly, the needle will remain in its drop position and not be advanced forward, and conversely, if the needle is moving on the conveyor, and the conveyor is stopped too quickly, the needle will continue to travel after the conveyor is stopped. The present apparatus seeks to avoid either of these situations by minimizing the amount of index at each incremental step while still providing enough movement to provide an adequate supply of needles to the apparatus.

In controlling the prior art device illustrated in FIG. 1(a), the needle singulating apparatus illustrated in FIG. 1(b) and FIGS. 3–5 provides a single needle at each drop point which substantially enhances the accuracy of the vision system and minimizes needle returns that might otherwise be necessary for overlapping or nested needles that were either not imaged, or selected by the computer control means 46 for transfer by the robotic apparatus 108.

The needles deposited on the translucent indexing conveyor 104 are imaged by a vision system 105 under control of a vision control task, and these images are processed by a computer control means 46 to identify the orientation and X,Y, and Z coordinate location of the needles. Determining the X,Y,Z coordinates alone is not enough in the needle swaging environment inasmuch as the robotic apparatus needs to determine, in the case of a symmetrically formed curved needle, which end is the barrel end and which end is the cutting end in order to properly place the needle for subsequent automated handling. Preferably, as will be described in greater detail, the vision control task additionally implements an algorithm to determine the orientation of the needle with respect to the gripper assembly of the robot, and specifically determines the location of the tip end and barrel end of the needle, as it is required that the robot gripper grip the barrel end during a pick operation. As shown in FIG. 4, there is employed a fixed mechanical finger 31, which, as shown in the side elevational view of FIG. 4(a), is a simple post 31a having a pin 31b extending outward therefrom. As shown in FIG. 4(b), when it is determined that the orientation of the picked needle is incorrect for proper placement of the needle in the engagement boat, the robot arm will be instructed to move to the location of the finger 31 and gently contact the needle against the finger pin 31b while simultaneously rotating to effectuate a "flipping" of the needle point approximately 180° while the barrel end is being gripped by the robot assembly 108. This flipping operation ensures that each needle is correctly oriented prior to being placed on the conveyor boat as conveyance of correctly oriented needles is necessary for the subsequent swaging operation. Furthermore, this manner of flipping the needle minimizes contact with the cutting edge such as may occur when a needle "plow" orientation mechanism is employed. It should be mentioned that the location of the mechanical finger 31 is dependent upon the type of movement that the robot is capable of, i.e., a location such that robotic movement toward the finger 31 is advantageous and can be accomplished swiftly without any mechanical stress.

After the robotic assembly 108 picks the needles from the translucent conveyors 102,104 and orients them by the mechanical finger 31, if necessary, it places them on a precision indexing conveyor 106. The precision conveyor 106 includes a plurality of "boats" 70 which are particularly adapted to convey uniformly oriented needles to the swaging dial for the subsequent swaging operation.

Specifically, the needles transferred by the robotic apparatus 108 are transferred so that the butt end of the needle 44 is engaged by gripping jaws on the conveyor boats 70 of the precision conveyor 106. While the butt end is located and gripped by the robotic apparatus 108, at the point of pickup it may be oriented in either direction of curvature. For larger non cutting-edge needles, a needle plow 111 is used to correct the direction of curvature. Both procedures may be employed simultaneously, since the needle plow 111 will only re-orient an incorrectly oriented needle. If the needle is oriented correctly, either by virtue of its original orientation on the belt, or by virtue of being "flipped" by finger 31, it will not engage the needle plow 111.

As illustrated in FIG. 4, the apparatus may include a pre-positioner 107 which is adapted to approximately locate the butt end of the needle and an moveable hard stop assembly at station 100 that precisely registers the butt end of the needle to an accuracy of 0.001 inches.

After the needle has been received at the precise positioning station 100, it is gripped transferred to one of the gripper devices, e.g., a universal gripper or multi-axis gripper, mounted on the rotary swage dial 130 and indexed at station 100. The rotary swage dial then rotates counter-clockwise as shown by the arrow in FIG. 6, to index each needle to the automatic swaging station 200 where the suture material is cut, inserted into the needle, and automatically swaged thereto. A suture drawing and cutting station 300 pulls, tips, cuts and inserts the suture into the needle to be swaged. The needle is swaged and then, the rotary swage dial 130 rotates to index the armed suture to the automatic pull-test station 400 where each armed needle is pull-tested to ensure that the minimum and/or destructive pull-test requirements of the medical profession, are met such as described in co-pending U.S. application Ser. No. 08/848, 927, now U.S. Pat. No. 6,012,216. Finally, the rotary swage dial indexes the pull-tested armed needle to the off-load station 500 where the surgical needle and suture assemblies are handed off for suture bundling for subsequent packaging at another location.

Generally, in the needle threading and swaging system, parallel operations take place simultaneously at a plurality of different stations to ensure that approximately forty to sixty (40–60) armed surgical needles are assembled and discharged per minute.

Semi-Automatic Needle Singulation

The needle singulation apparatus, the operation of the indexing conveyors 102,104, the robotic apparatus 108, the precision conveyor 106 and the moveable hard stop will be described with respect to FIGS. 7 through 12.

Referring to FIGS. 7(a),(b), the semi-automatic needle singulation apparatus includes a singulation or needle sliding surface 50 on table 53 which assists an operator in singulating needles that are deposited on the table surface in bulk. While it is well known that it is difficult to pick up a needle from a flat surface, it has been found that an operator may singulate and slide a needle quickly to a drop point, such as needle drop points 48 and 49 to provide a singulation function. These drop points are openings in the singulation surface 50, which open to horizontal channels 55,56 formed in needle block 57, illustrated in partial cross section in FIG. 7(b). Channels 55,56 open to drop openings 58,59 above the translucent indexing conveyors 102,104. When the operator slides a needle to the drop opening 48, it falls a distance of 0.51" to 1.0" to the staging surface of channel 55 immediately under the drop opening 48. It is transferred from the staging surface to the second opening 58 in channel 55 by a puff of air from channel 60. Air channel 60 extends upwardly through the needle block 57 and opens in both directions, with a first opening aligned with channel 55, and a second opening aligned with channel 56. As the translucent conveyor is indexed, a solenoid opens the air supply to air channel 60, creating a puff of air in both directions which blows any needles on the intermediate staging surfaces through the channels, and out the lower openings 58,59 to the translucent conveyors 102,104. The needle block is preferably formed of delrin, although other materials would be suitable, provided the material is not soft enough to let the needle points inadvertently dig in. The semi-automatic singulation avoids needle to needle contact inherent in the vibratory feed bowls illustrated in U.S. Pat. No. 5,568,593 and thus substantially reduces the risk that premium needles or cutting edge needles will be blunted by needle to needle contact.

The semi-automatic operator work station includes a platform 51 for operator seating and guard rails 52 for operator safety. Safety guards 54 are also provided around the machine for safety purposes. CRT supports 61a and 61b are also provided to enable the operator to monitor the automatic operation of the apparatus through suitable computer CRT displays.

As will be hereinafter explained in greater detail, the indexing conveyors are alternately indexed a distance of approximately 2" at every index, and this alternate operation and the close spacing of drop openings 48,49 enable an operator to singulate 30 to 60 needles a minute, so that only a single needle is deposited at each incremental advance of the indexing conveyors 102, 104.

The needles are then advanced by the indexing conveyors to imaging stations 101,103 (FIG. 4) to be imaged by the vision system. The robotic and vision control system will be hereinafter described in greater detail with respect to FIG. 8. The individual needles are imaged and data representing both their x,y and z position and their orientation is obtained by the vision control system. The orientation data is needed since the correct end of the needle must be presented when the needle is handed off for automatic swaging.

As described above, and as illustrated in FIGS. 3–5, the robotic assembly 108 is located downstream from the needle singulating station and proximate to both of the translucent indexing conveyors 102, 104 and the precision conveyor 106. In the preferred embodiment described herein, the robotic assembly 108 is an Adept® 550, 4-axis robot capable of accomplishing needle transfers at a rate of approximately 40–60 transfers per minute as controlled by the robot's corresponding Adept® MV controller. Each robot is a four-axis SCARA (Selective Compliance Assembly Robot Arm) robot comprising four Joints capable of a variety of motion. Robotic grippers 109 are attached to the quill of the robot assembly 108 and are enabled to provide gripping action by pressure supplied from an air cylinder (not shown).

Referring now to FIGS. 4 and 10, there is illustrated the precision conveyor 106 which is driven by drive motor assembly 62 at a rate sufficient to index and transfer one oriented surgical needle at a rate of up to one per second (1 needle/sec) to the automatic swaging apparatus. A similar drive motor assembly is provided for driving the indexing conveyors 102,104. As will be explained in detail below, each of the drive motor assemblies are interfaced with and operate under the control of a control system 46 and employs programmable logic controllers ("PLC's") in digital communication with the Adept® MV robot controllers and the vision tracking system components to control the infeed system. Particularly, the PLC's receive control signals from the MV controllers to effectuate pausing of the indexing translucent conveyor at the desired cycle rate to enable the vision system to locate a needle position for subsequent robot pick-up thereat, and further, to control the indexing of the precision conveyor for robotic transfer of the needle from the indexing conveyor to the precision conveyor.

Figure 10A:
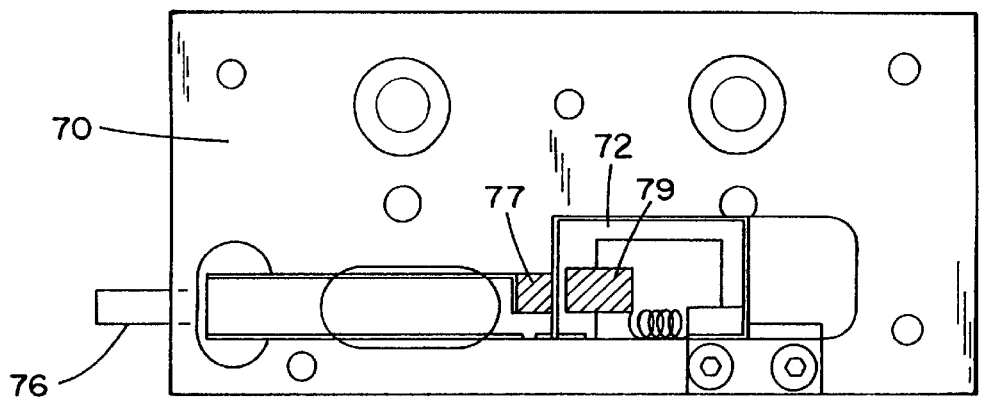
FIG. 10(a) is a partially cross sectioned plan view of one of the conveyor "boats" used by the precision conveyor of the present invention.
Figure 10B:
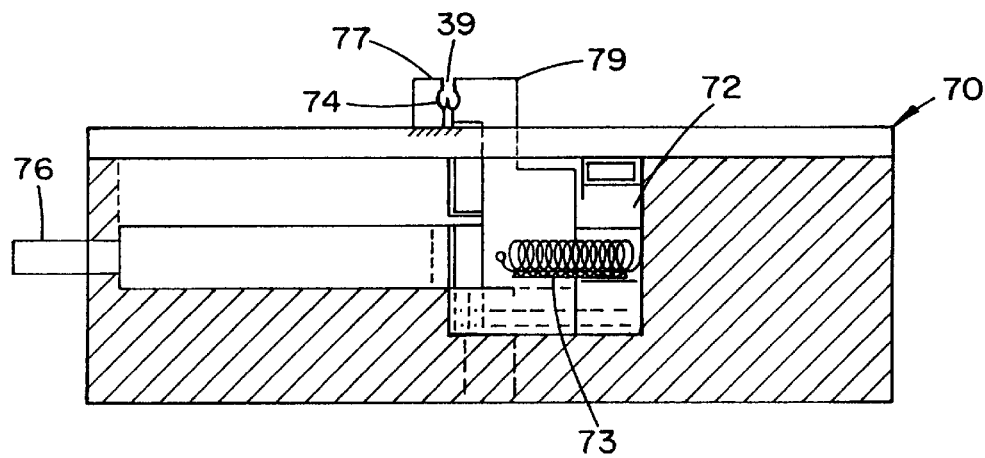
FIG. 10(b) is a partially cross sectioned elevation view of one of the conveyor "boats" used by the precision conveyor of the present invention.
Figure 10C:
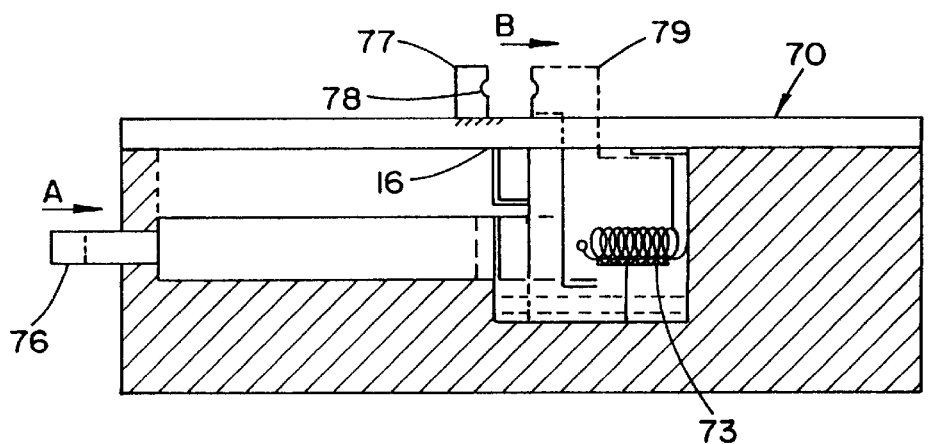
FIG. 10(c) is a partially cross sectioned elevation view of one of the conveyor "boats" used by the precision conveyor of the present invention, with the jaws thereof in an open position.

FIGS. 10(a), (b) and (c) illustrate in detail one of the plurality of engagement boats 70 located on precision conveyor 106 for engaging respective individual surgical needles 39. Each boat is preferably provided with a pair of jaws; one jaw 77 being fixedly mounted, and the second jaw 79 being slidable within cavity 72. In operation, a push rod 76 is pressed in the direction of the arrow "A" shown in FIG. 10(c) to compress spring 52 which retracts the position of the movable jaw 79 in the direction indicated by the arrow "B" to allow for placement of needle 39 within the notch 78 of both jaws. Normally, spring 73 is biased as shown in FIG. 10(b) to maintain movable jaw 79 in its engaged position for retaining a needle 39 in the notch 74. It should be understood that any type of releasable engaging mechanism may be provided for releasably retaining a needle 39 on conveyor boat 70, provided that each needle be correctly oriented on its respective boat for subsequent swaging to take place.

As shown in FIG. 4, the vision tracking system comprises a camera assembly 105 having two video cameras each located overhead a respective illuminated platform portion, 101 and 103, of the indexing conveyors 102,104. As will be explained in detail below, the video images of the needles obtained from each camera 105 are bit-mapped or suitably digitized and transmitted via suitable transmission or communication lines to the MV controller where the Vision Control task processes the video images and supplies needle location and orientation data to the robotic assembly 108. Preferably, the conveyors 102 and 104 are translucent and are backlit at the respective portions 101 and 103 so that a sharp video image may be obtained by the overhead camera assembly for processing. It is understood that for descriptive purposes, two video cameras 105 corresponding to the two illuminated platforms 101,103 are shown in FIGS. 4 and 5.

The through-put and redundancy designed into this vision system ensures that there will be no momentary shortage of needles fed to the swaging station and that maximum throughput of oriented needles for input to the swaging station is achieved. Furthermore, a robotic assembly of sufficient speed and precision may, in the future, be able to pick up randomly deposited needles from a moving conveyor and place them directly in an oriented position at the swaging station.

In the preferred embodiment, each camera 105 is mounted approximately one (1) meter above each backlit indexing conveyor imaging area 101,103 and utilizes an electrically controlled telephoto lens with a focal distance ranging from 10 mm to 140 mm that may be changed with suitable adaptors. Suitable lens controllers are used to establish lighting/iris, focus, and field of view for each camera lens, and, are interfaced with the vision system via an RS-232 link.

A further component of the control system for the needle sorting and infeed apparatus includes an SCADA Node which is used to oversee and direct the infeed system. This node interfaces with the Adept® controller via discrete RS-232 links which are used to download data information, such as needle parameters, error messages, and status messages, to the Adept® controllers. The SCADA node may comprise a personal computer or such suitable device, running commercially available FIX/DMACS® software. Serial communication is used to exchange the needle parameters entered at the FIX/DMACS "Adept® Setup" screen during a needle changeover procedure which is used to inform the infeed system of the size and type of needles to be processed. After an operator enters the needle parameters and initiates a changeover, the FIX/DMACS Node will transmit these parameters to the robot controller(s).

The Robotic and Vision Control System

Figure 8:
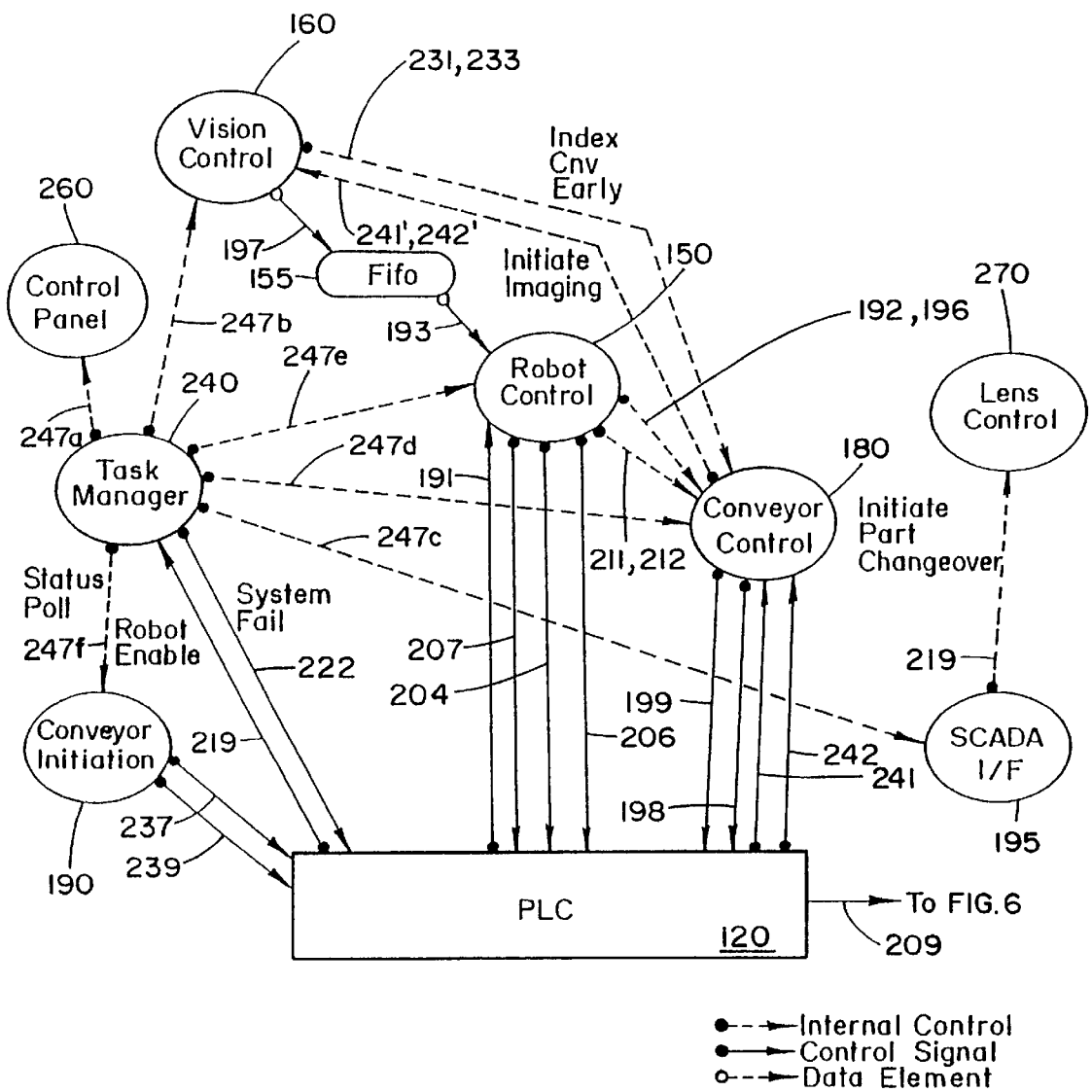
FIG. 8 is a state or task diagram of the imaging system used to obtain position and orientation data of individual needles for the robotic system used by the present invention.

The robotic/vision computer control system 300 of the invention is illustrated in the state or task diagram of FIG. 8. As illustrated, the computer control system 300 comprises individual computer software programs, each associated with a particular task to be performed by various assemblies of the apparatus and executed under the control of the PLC 120. As shown in FIG. 8, the software architecture for controlling the needle sorting apparatus of the instant invention performs eight (8) main tasks: a Robot Control task 150; a Vision Control task 160; a Conveyor Indexing Control task 180; a SCADA Node Interface task 195; a Control Panel task 260; a Task Manager 240; a Conveyor Initiation task 190; and, a Lens Control task 270. Of these eight tasks mentioned above, the first six are active during steady state operation as will be explained below. FIG. 8 additionally shows the data flow among the tasks and the signals which initiate the tasks. It is understood that the control programs are written in Adept's V/V+ language, operating under control of the V+ operating system which supports both vision and robotic control in a multitasking environment.

It should be understood to those skilled in the art that the robotic assembly, controller, and camera vision tracking system requires calibration and configuration procedures for the system to properly function. For instance, the robotic assembly requires that joint positions be set and joint limits be configured to ensure that the robot avoids structural damage when enabled. Furthermore, a camera-to-robot calibration is required so that the vision system may accurately compute the positional coordinates of the needle so that the robot may move to the pick position. This procedure provides a translation matrix between the camera's field-of-view and the robot base position.

The PLC 120 is responsible for initially powering the robot controller and the robotic assembly. A robot calibration procedure may be initiated after power-up to move the robot joints to known "home" positions to synchronize the digital encoders of the assembly.

The process of starting the PLC 120, robot controllers, indexing conveyors 102, 104 and precision conveyor 106 is time-critical. From the robot controller perspective, when a ROBOT ENABLE signal 219 is raised by PLC 120, it begins its normal cycle by executing the Robot Control Task 150, the Vision Control Task 160, the Conveyor Indexing Control Task 180, and the Conveyor Initiation Task 190; which initiates the movement of indexing conveyor 102, waits approximately up to two (2) seconds, and then initiates the movement of second indexing conveyor 104 as will be described in detail below. Under this scenario, the PLC integrates the startup of the Indexing Conveyors, and swaging machine with the raising of the ROBOT ENABLE signal 219. As will be explained in further detail below, when the ROBOT ENABLE signal goes low, the Adept robot halts its standard processing and responds to requests from the SCADA node.

Robot Control Task

There is a single Robot Control task associated with the Adept® MV controller for the robotic assembly 108, indicated as element 150 in FIG. 8. The control system software for the Robot Control task 150 manages the robotic assembly 108 as a resource, reads a FIFO buffer 155 of identified needle locations which are produced by and input from the Vision Control Task 160, interfaces with the programmable logic controller (PLC) 120 and control system 46 for needle placement handshaking, and, initiates the indexing of the conveyors 102 and 104.

As shown in the block diagram of FIGS. 9(a)–9(c), the steady state operation of the Robot Control task 150 for the robot assembly 108, is as follows:

First, the robot controller 150 continuously polls its input FIFO 155 via data line 193 to obtain positional coordinate data for the selected needle locations on a respective translucent conveyor 102 or 104 as indicated as step 302. The data for the needle locations are provided to the FIFO buffer from the Vision Control task 160 via respective data lines 197 as will be explained in further detail below. As will be explained, the Vision task performs a unique analysis of the needle image on the translucent conveyor to determine which edge is the cutting or barrel end of the needle. Once it is determined which end is the barrel end, the Vision control task 160 downloads the positional coordinates that will locate the robot gripper location parallel to the barrel end of the needle. The Vision control task additionally examines the orientation of the needle and provides rotational information to the robot. Thus, two separate orientation parameters are determined. First, a determination is made as to which end of the curved needle is the barrel end, as explained in detail herein with respect to FIG. 9(g), and secondly, a determination is made as to the rotational orientation of the needle, as explained in detail herein with respect to FIG. 9(f). The robot controller will remove the needle position and orientation data from the buffer and command the robot gripper 109 to move to that pick location at the translucent conveyor belt as indicated at step 304. Particularly, at step 304 the control system enabling robot arm pick and place movement invokes a first routine (not shown) enabling the robot to approach the pick location with specified motion parameters (approach location, approach height, acceleration of approach, deceleration of approach, speed of approach); and, a second routine for enabling the robot to move to the approach location with specified motion parameters (the type of movement, acceleration of move, deceleration of move, speed of move, and brake or pause movement if the robot is supposed to brake (pause) after moving).

The robot control task then makes a determination at step 306 as to whether the needle is a cutting edge needle. If the needle is not a cutting edge needle, the Robot Control task 150 will signal the robot gripper 109 to close on the needle barrel portion 44 and to depart from the conveyor belt at the specified motion parameters including acceleration of depart, deceleration of depart, speed of depart, pausing or braking, etc., as indicated at step 312, FIG. 9(b), for movement to the needle place location at the precision conveyor 106 for needle transference thereof.

If, at step 306, FIG. 9(a), it is determined that the needle is a cutting edge needle, then at step 308 a determination is made as to whether the needle tip will be facing in the direction of the front conveyor 104 or the back conveyor 102, once picked by the robot gripper. Specifically, this determination is made given the rotational orientation data of the needle as provided by the Vision task, in the manner described. If it is determined that the needle is a cutting edge needle and the tip of the needle will be facing in the direction of the front conveyor 104 once gripped by the robot gripper, (i.e., the needle tip faces the left side of the gripper) the process will continue at step 312, FIG. 9(b) where the Robot Control task 150 will signal the robot gripper 109 to close on the needle barrel portion 44 to grip the needle and depart in accordance with the specified motion parameters from the conveyor to a placement location at a precision conveyor boat for needle transference thereto. If it is determined at step 308 that the needle point is rotationally oriented such that the needle will be facing in the direction of the back conveyor when gripped by the robot gripper, (i.e., the needle tip faces the right side of the gripper), then the Robot 108 will pick-up the needle and move the needle to the location of the mechanical finger 31 (FIG. 4(a)) to rotate the orientation of the needle point, as indicated at step 310. Specifically, when needle flipping of the needle is required at step 310, the robotic control system will invoke the first (approach) and second (move) routines to move the robot gripping needle to the needle flip location where the mechanical finger 31 is located (FIG. 4), and, in the manner described above with respect to FIG. 4(b), contact the needle against the pin and rotate in the direction indicated by the arrow shown in FIG. 4(b) to change the orientation of the needle. After the needle has been flipped by the robot gripper, it will depart to the placement location at a precision conveyor boat in accordance with the specified motion parameters. The process then continues at step 313, FIG. 9(b).

Figure 9C:
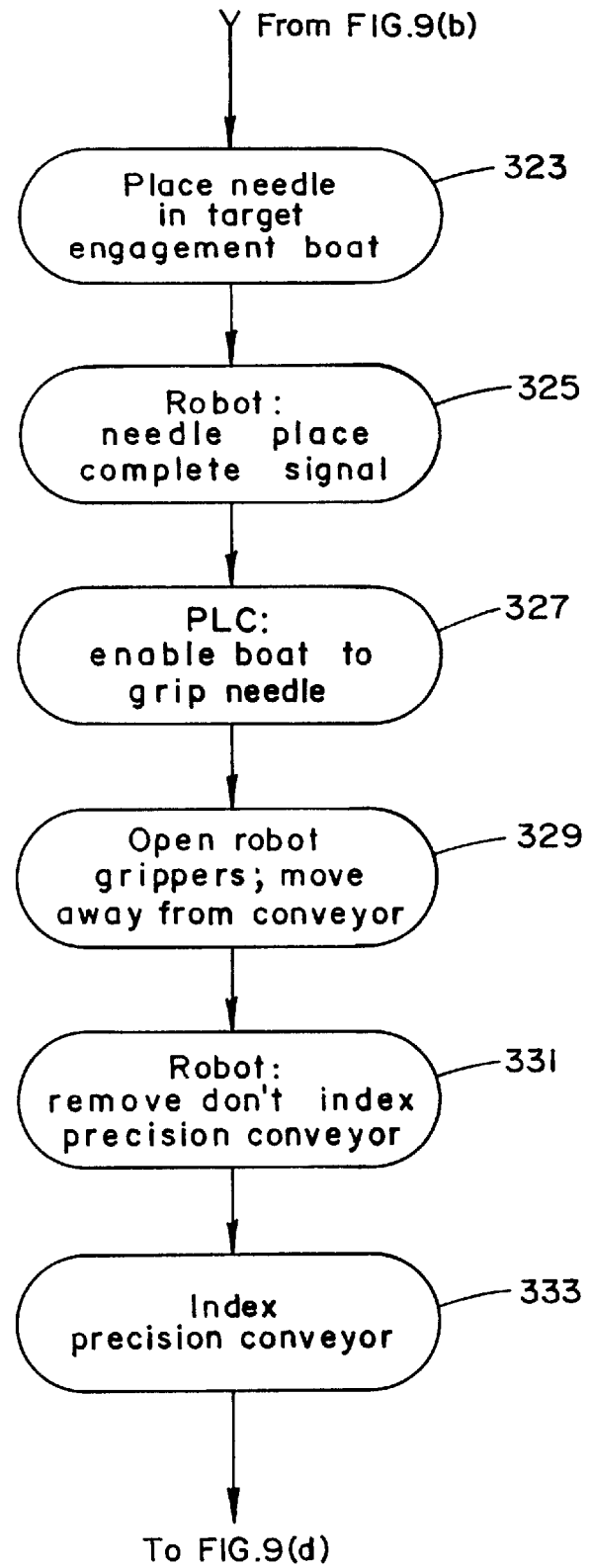

At step 312, FIG. 9(b), the robot control task then generates a NEEDLE IN GRIPPER signal 207 to the PLC as indicated and waits for a response from the PLC 120. As shown as step 315 in FIG. 9(b), and, in further view of FIG. 8, when the PLC receives a NEEDLE IN GRIPPER signal 207, the PLC 120 will generate a SAFE TO PLACE signal 191 for receipt by the robot 108. The purpose of the SAFE TO PLACE signal 191 is to inform the robot assembly 108 that a needle may be placed onto a precision conveyor boat 70 of conveyor 106. As a response to the receipt of the SAFE TO PLACE signal 191, the Robot Control task 150 will generate a DON'T INDEX PRECISION CONVEYOR signal 204 at step 317 for receipt by the PLC 120 immediately before it places the needle on the precision conveyor 35. While this signal remains high, for e.g., at a logic "1" state, the Adept® robot assembly 108 will place a needle onto a boat 70 of precision conveyor 106 as indicated as step 323 in FIG. 9(c). This involves initiating the engagement jaws 77,79 of the precision conveyor engagement boat 70 to retract to allow the placement of the needle therebetween.

Figure 6:
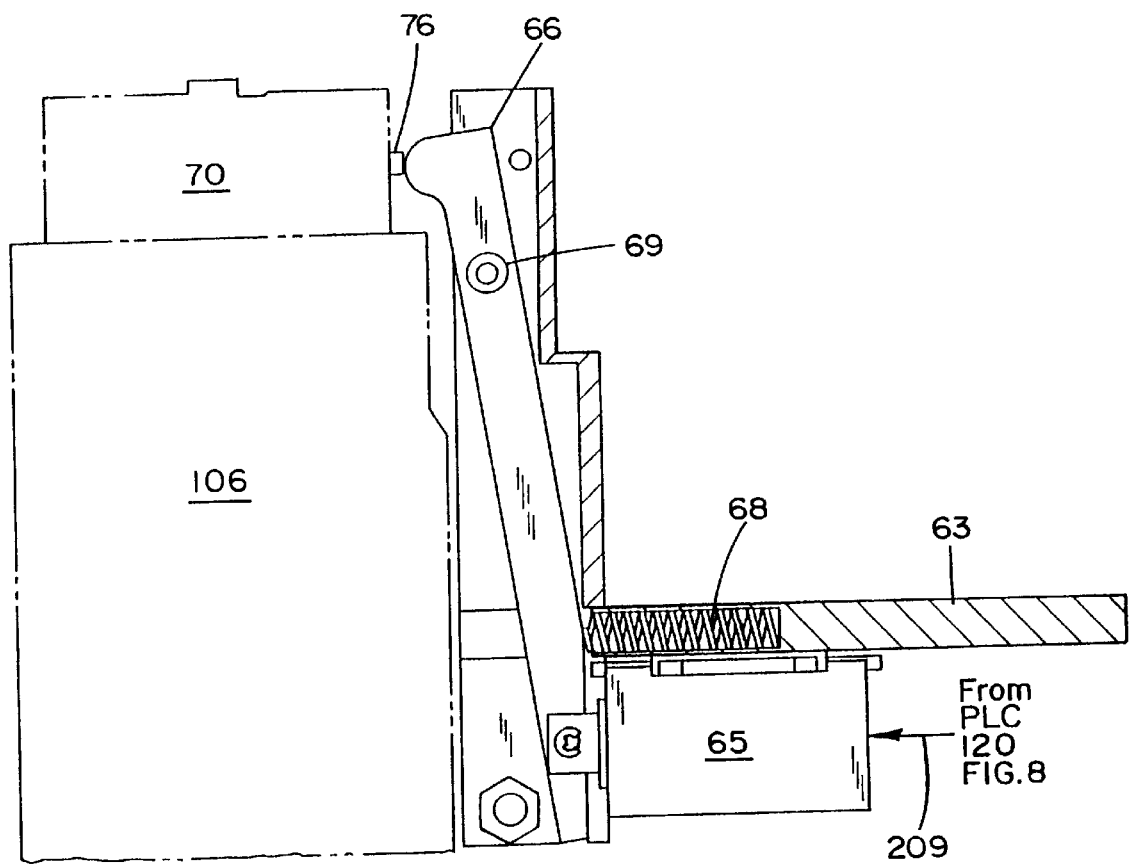
FIG. 6 illustrates a detailed side view of the robot load solenoid that actuates the jaws of the precision conveyor boat.

Particularly, FIG. 6 illustrates a robot load solenoid mechanism 65 that is activated by the PLC 120 each time a needle 39 is being transferred to a precision conveyor boat 70 as described with respect to step 323 of FIG. 9(c). The robot load solenoid 65 may be mounted to the precision conveyor by an appropriate mounting plate 63. A sensor mounted on the precision conveyor, is also provided to sense the proximity of the precision conveyor boat 70. At such time a conveyor boat is dwelled for transference of a needle 39 thereto, a release arm 66 of the robot load solenoid is actuated by solenoid 67 at the initiation of the PLC 120 to pivot about pin 69 to depress push rod 76 and retract the movable jaw 79 to the position illustrated in FIG. 10(c). The robot gripper 109 then positions the needle 39 between the jaws 74,79 of conveyor boat 70 for engagement thereof as explained above with reference to FIGS. 10(a)–(c).

Once the movement of the robot has settled and a needle is placed, the Robot task 150 will generate a NEEDLE PLACE COMPLETE signal 206 for receipt by the PLC 120 at step 325, and, the PLC will generate a suitable control signal 209 to enable the engagement jaws of the precision conveyor engagement boat 70 to engage the needle at step 327. This involves retracting release arm 66 by spring 68 of the load solenoid mechanism as shown in FIG. 6. In the preferred embodiment, the dwell time of the NEEDLE PLACE COMPLETE signal 206 is approximately 48–64 milliseconds. After activating this signal, the robot assembly 108 will hold the needle in place for the same time period. (48–64 msec.) Immediately thereafter, the robot will open its grippers and move away from the engagement boat 70 for approximately 4 mm in the direction in which it approached the place position in accordance with the specified depart movement parameters as indicated as step 329 in FIG. 9(c). The robot arm then moves away from the conveyor 106 in accordance with the specified robot movement parameters. Finally, the DON'T INDEX PRECISION CONVEYOR signal 204 is removed at step 331 indicating that it is now clear for the PLC (and Conveyor Control task) to initiate the indexing of the precision conveyor 106 which is performed at the command of the PLC 120 at step 333 in FIG. 9(c).

Referring back to FIG. 8, as a safety interlock for conveyor index initiation, the Robot Control Task 150 will signal the Conveyor Indexing Control Task 180 with an internal control LAST PICK signal 192, 193 indicating that the robot assembly 108 has picked up the last needle from the current conveyor as indicated. If the maximum number of needles expected per camera field-of-view ("FOV") is not picked from the respective current infeed conveyor 102, 104, the Robot Control Task 150 will request the Conveyor Control task 180 to index that conveyor belt "early" via the INDEX CONVEYOR 1 EARLY or the INDEX CONVEYOR 2 EARLY signals 211,212, respectively, as shown in FIG. 8. Since all signals affecting the motion of the conveyors are routed through the Conveyor Control task 180, the Conveyor Control task will generate a corresponding INDEX CONVEYOR 1 EARLY, signal 211 or INDEX CONVEYOR 2 EARLY, signal 212, for receipt by the Adept robot. If during normal operation a Robot Control Task receives either Index Conveyor I Early or the Index Conveyor 2 Early signal, it will flush the contents of its FIFO buffer 155 and continue as if the last needle has been picked from the conveyor.

The control software must take into account the floating 16–32 ms duration of a digital output based on the time slicing of V/V+. This will affect the calculation for minimum time required for placement in conjunction with setting and resetting the Don't Index Precision conveyor signal 204.

The Robot Control Task 150 performs error recovery on two type of errors. These errors are grouped as indexing errors and gross errors. As in all other tasks, gross errors cause the Task Manager 240 error recovery to respond and stop the Robot Control Task immediately. An indexing error occurs if a robot is waiting for a needle to be placed in its parts FIFO and both conveyor belts have not indexed within an appropriate amount of time. The Robot Control Task 150 recovers from this type of error by requesting the other robot to index early via INDEX CONVEYOR I EARLY (signal 211) or INDEX CONVEYOR 2 EARLY (signal 212). This forces both vision robot control systems to flush the contents of its current parts FIFO and index the conveyor belts.

Although, the invention is particularly advantageous when employed in the semi-automated singulation method employing one robot apparatus, it is contemplated that the invention may be employed in semi- or fully automated systems employing two robot assemblies, e.g., in the manner as described in the aforementioned U.S. Pat. No. 5,568,593.

Conveyor Indexing Control Task

The Conveyor Indexing Control Task 180 initiates the indexing of each respective translucent indexing conveyor 102, 104 and the task is initiated by the Conveyor Initiation task 190. All signals affecting the motion of the conveyors are routed through the Conveyor Control task 180, the flow diagram of which is illustrated in FIG. 9(d).

Figure 9D:
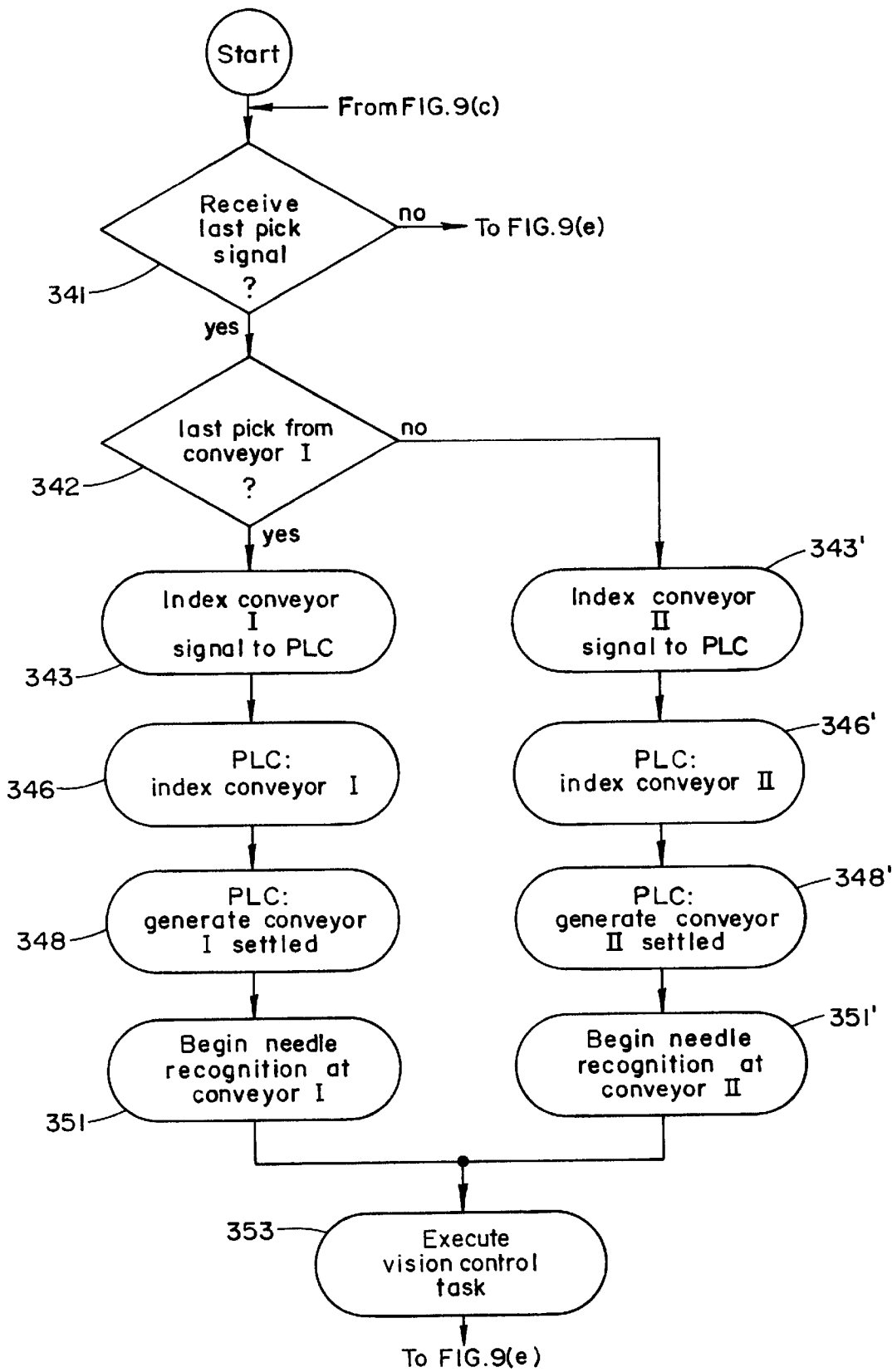

As shown in FIG. 9(d), and in further view of FIG. 8, the first step 341 of the Conveyor Indexing Control task 180 is to check for the LAST PICK signal 192,193 internally generated from the Robot Control Task 150 and indicating that the last needle pick-up from the respective infeed translucent conveyor 102, 104 has been completed by the Adept® robot 108. Alternatively, the Conveyor Indexing Control Task 180 awaits for the INDEX CONVEYOR EARLY (1 and 2) signals internally generated by the Vision Control task 160 when no needles are recognized in the current camera field of view. Thus, as shown at step 342 in FIG. 9(c) the determination is made as to whether the Adept robot has initiated the LAST PICK signal from Conveyor 1. As a result of receiving the LAST PICK signals 192,193 from the robot task, the Conveyor Control task will generate a corresponding INDEX CONVEYOR 1 signal 198, or, an INDEX CONVEYOR 2 signal 199, for receipt by the PLC 120, as indicated as respective steps 343 and 343' in FIG. 9(d). It is essential that the Adept® robot controller must request the PLC 120 to index a translucent indexing conveyor 102, 104 after picking up the last needle from the respective conveyor. This signal will cause the corresponding conveyor 102, 104 to generate to abort processing and initiate indexing of the belt.

After receipt of either INDEX CONVEYOR I (or INDEX CONVEYOR 2 signals 198,199 from the robot assembly, as shown at steps 346 and 346', the PLC 120 commands the respective translucent indexing conveyor 102, 104 to index, and, at steps 348 and 348', generates a corresponding CONVEYOR 1 SETTLED signal 241 or, a CONVEYOR 2 SETTLED signal 242 for receipt by the Conveyor Control Task 180. Note that the CONVEYOR 1 SETTLED signal 241 and the CONVEYOR 2 SETTLED signal 242 are raised approximately 2 seconds after the PLC has been requested by the robot control task 150 to index conveyor 102, 104. The Conveyor Control Task 180 then informs the Vision Control task 160 to begin needle imaging upon receipt of internal control signals 241',242' that correspond to the respective CONVEYOR I SETTLED or the CONVEYOR 2 SETTLED signals 241, 242. Once the indexing conveyor 102, 104 has been indexed and the corresponding CONVEYOR SETTLED signal 241,242 has been received, the Vision Control Task 160 may begin needle recognition in the corresponding cameras's FOV, as indicated at step 351 and 351' in FIG. 9(d). Specifically, under the control of the Vision Control task 160, the cameras 105a,b of the recently indexed conveyor 102, 104 will take a snapshot of the respective field of views at illuminated portions 101,103 thereof, and the task will process the image to make a determination of whether recognizable needles are present in each camera's field of view as indicated at step 353 in FIG. 9(d).

At this point, a distinction must be made between the mere presence or detection of a needle in the field of view and the presence of a "recognizable" needle. A needle may be present, but, for a variety of reasons, the Vision Task 160 may not be able to determine its positional and orientational coordinates until the camera vision parameters are changed by the execution of an auto-imaging algorithm which automatically adjusts the iris and vision system lighting parameters of each camera so that the cameras may subsequently obtain enhanced images that may be processed. During steady state, when the vision task has already "recognized" a needle in its respective field of view, the auto-imaging algorithm is not repeated. Details of the auto-imaging algorithm will be explained in detail below.

Vision Control Task

The Vision Control Task 160 controls and processes the images taken by each of the two camera assemblies 105a, 105b. Since the timing of the two translucent conveyors are phased, only one camera is operating at one time. Specifically, as shown in FIG. 4, the Vision Control task 160 interfaces with each camera 105a,105b to identify the needle locations of recognizable needles in that respective camera lens's field of view encompassing an area located at respective illuminated platforms 101,103. The Vision Task 160 then processes the positional and rotational orientation information of the identified needle location and downloads those locations to the Robot Task FIFO 155 via data lines 191. As mentioned above, the Vision Control task is additionally responsible for initiating an early conveyor index if no needles were imaged in a camera field of view.

As described briefly above, the Vision Control task runs each time either conveyor 102, 104 completes indexing. It is initiated to begin needle recognition upon receipt of either internally generated CONVEYOR I SETTLED signal 241' or CONVEYOR 2 SETTLED signal 242' which is generated by the PLC 120 and routed through the Conveyor Control task 180 each time respective translucent indexing conveyor 102, 104 has ceased indexing. Each CONVEYOR SETTLED signal 241,242 goes high (Logic "1") approximately two (2) seconds after the PLC has been requested by the Adept® robot to index a translucent indexing conveyor.

Each of the CONVEYOR SETTLED signals 1 and 2 (241, 242) remain high until the PLC 120 receives the next respective INDEX CONVEYOR 1 or 2 signal 198,199 from the Robot Control and Conveyor Control tasks.

Figure 9E:
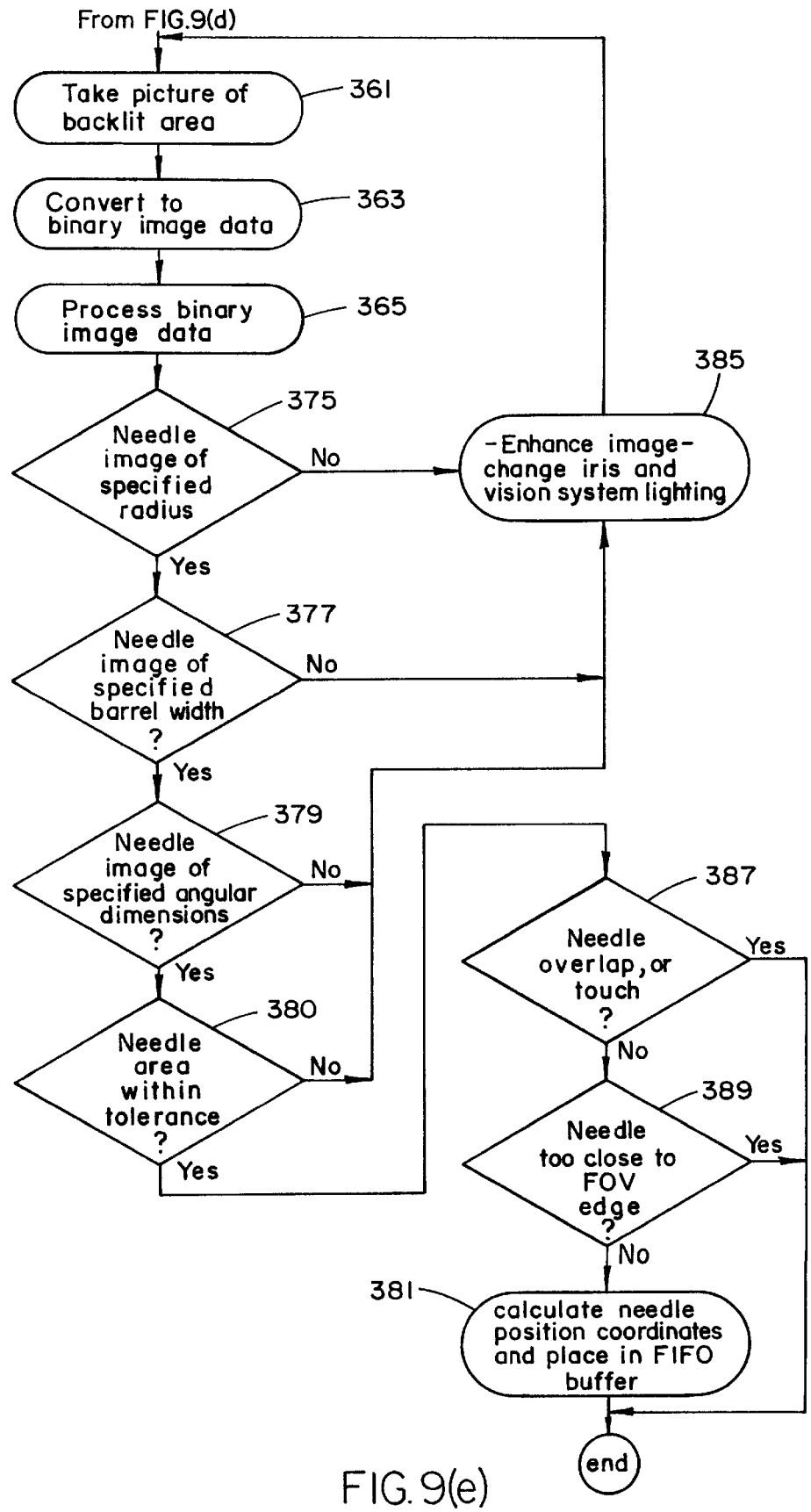

As illustrated in FIG. 9(e), the Vision Task 160 activates that camera which is associated with the conveyor settled signal. When activated, the camera 105,105a takes a picture of the backlit areas 101,103 of the conveyor belt 102, 104 as indicated at step 361. Any image obtained is preferably converted to binary image data as indicated at step 363 for subsequent digital processing, indicated at step 365. The Vision Control task 160 utilizes "vision tools" to detect acceptable needles, and enqueues the coordinates location of the acceptable needle pick-up point and FOV location in the FIFO buffer 155 for the Robot task. An "acceptable" needle in the backlit areas is a needle that measures within the tolerances of the needle parameters that have been previously accepted during a needle changeover procedure which is a procedure to inform the infeed system software of the type and size of the needles in the current batch to be processed. Specified needle tolerances are for the needle radius, barrel width, angular characteristics of the needle with respect to the robots, and the calculated area as computed from the needle parameters.

Auto-Imaging Algorithm

As mentioned above, if a detected needle is unrecognizable after a needle changeover, the auto-imaging algorithm is invoked to change the camera vision parameters. Thus, after the binary image data is processed at step 365 as shown in FIG. 9(e), a determination is made as to whether the needle image is of the specified radius (step 375), whether the needle image is of the specified barrel width (step 77), whether the needle image has the specified angular characteristics (step 379), and, whether the needle image area is within the specified tolerance (step 380). If any of these criteria are out of specification, then a routine for optimizing the binarly threshold is executed at step 385. The function of this routine is to enhance the needle image for better needle recognition by taking one or more pictures of the same needle image at the respective camera's field of view. Thus, as shown in FIG. 9(e), image enhancement parameters are changed and the process returns to step 361. Thus, after each of the series of pictures is taken, the auto-imaging algorithm will automatically adjust the camera's iris and vision system lighting parameters to enable the vision system to image the needles properly within the camera's field of view. For example, when adjusting the lighting of the fields of view, certain camera vision parameters such as the gain, offset, in addition to the binary threshold may be modified. The auto-imaging algorithm is only executed once after completing a needle changeover.

Even when the cameras of the Vision Control task 160 are adjusted, needle images may still not be imaged properly. This is because each camera's field of view utilizes a backlighting source and needles that overlap, touch with each other, or, are clipped by field of view edge boundaries will not be considered for recognition. Thus, as indicated in FIG. 9(e) at step 387, the Vision Control task will make a determination of whether the needles overlap or touch each other, and, at step 389, will determine whether the needles are too close to the edge of the field of view.

After all of the possible needles are recognized, the Vision Control task will calculate the needle pick-up coordinates of the acceptable needles and place them in the Robot Control task FIFO buffer 155 (FIG. 8) to enable the robot to pick and place the acceptable needle onto the precision conveyor, as indicated at step 399. In the preferred embodiment, the maximum number of needles that can be recognized during each dwell cycle of each translucent indexing conveyor is three (3). If less than this maximum or if no needles are recognized, a robot may be signaled to index the corresponding conveyor early, causing the vision system to abort its processing as described above.

Vision Task 160 is responsible for limiting the number of needle locations written to the FIFO to three, since the Robot Control Task will pick and place a needle for every needle location passed to the FIFO 155. In the preferred embodiment, the Vision Task is limited to operate for five seconds per indexing conveyor cycle.

Figure 9F:
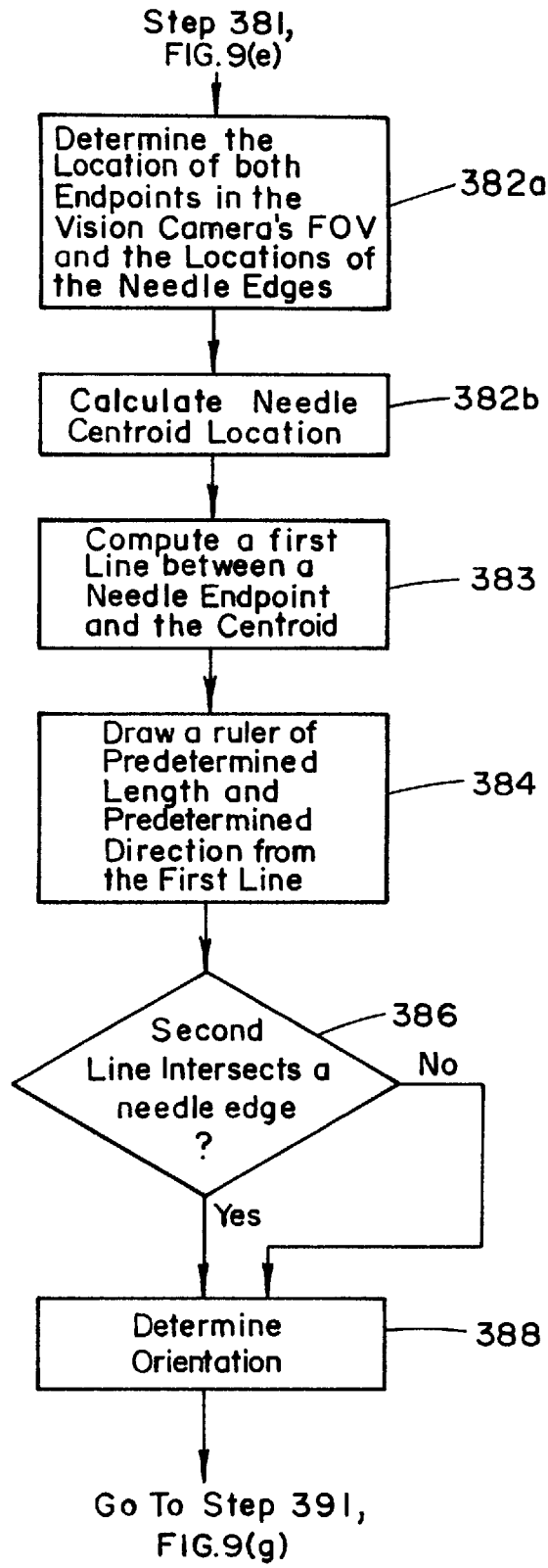
Figure 9G:
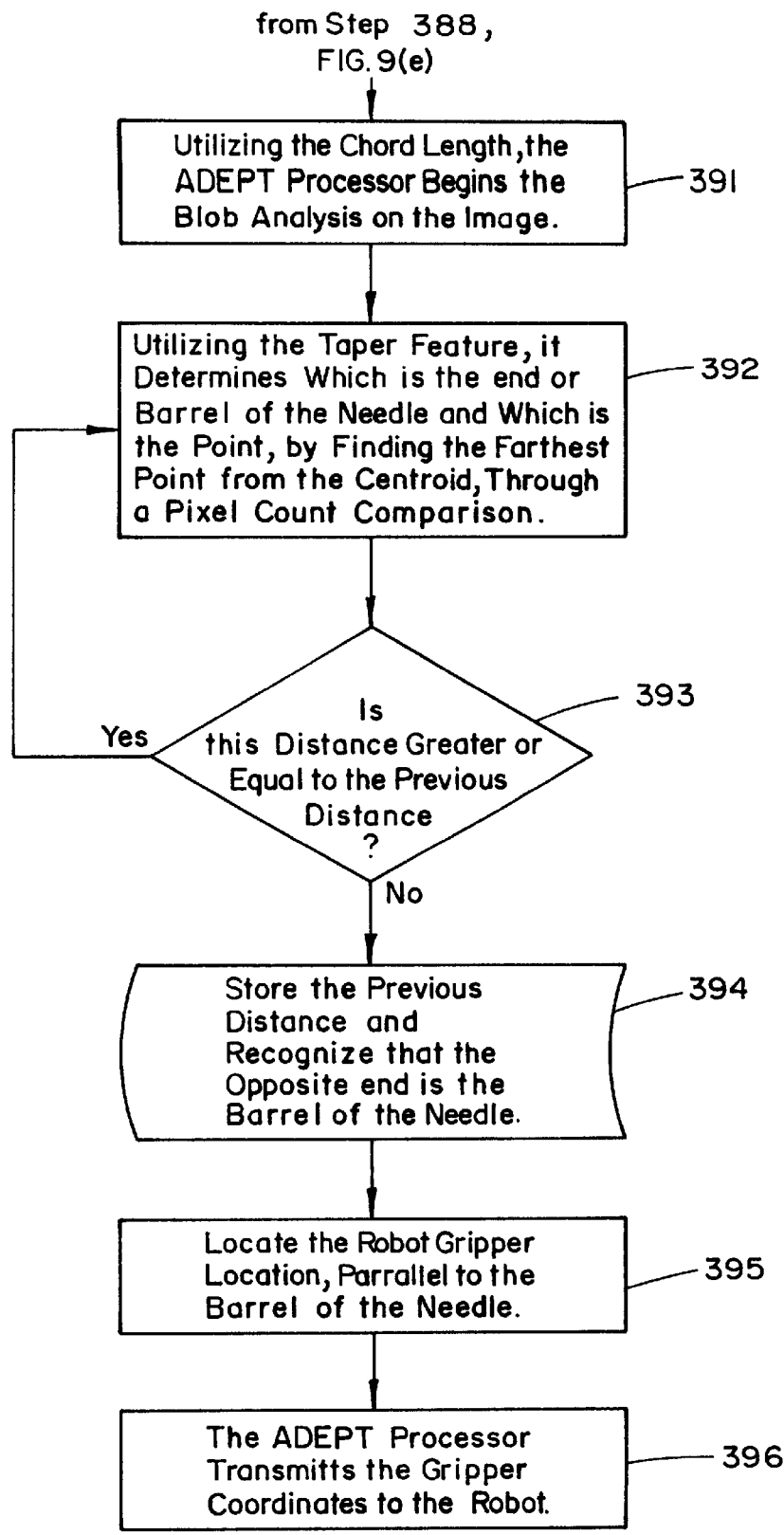

FIG. 9(f) illustrates the processing at step 399 for determining the needle orientation and FIG. 9(g) illustrates the process steps for differentiating which end of the imaged needle is the point end and which is the barrel end from the binary image data as executed by Vision control task 160.

To determine needle rotational orientation, the Vision task software implements the following steps as shown in FIG. 9(f): 1) it determines the location of both endpoints in the vision camera's field of view as shown at step 382(a), and, determines the locations of all of the needle edges; 2) it calculates a predetermined location associated with the needle, which, in the preferred embodiment, is the needle centroid location, as indicated at step 382; 3) it computes a first line capable of intersecting a needle endpoint (whether it be the barrel or tip end) and the predetermined location, as indicated as step 383; 4) it computes a second line of predetermined length and predetermined direction drawn from the first line, as indicated as step 384; and 5) it determines whether the second line intersects a needle edge as indicated at step 386. If it is determined that the second line does intersect a needle edge, then the needle rotational orientation is determined at step 388 based upon the intersection and the camera's FOV.

Continuing at FIG. 9(g), as indicated at step 391, the Vision control task then implements an algorithm to determine a cord length of the imaged needle, and at steps 392–394, implements a pixel count comparison technique for distinguishing the barrel end of the needle from the point end. That is, at a predetermined length from each needle end, a set of successive scans are made in the vision task software to slice the needle and determine the respective distances, i.e., widths, of the needle edges at each scan slice. In this manner, a maximum thickness and minimum thickness variation could be found at each needle end with the ratio of these values determining an overall maximum thickness variation for each end. It is this ratio will determine the amount of taper at that particular needle end. It should be understood that this procedure is performed at a high speed requiring minimum calculations. Once a taper ratio is determined for each end point, a comparison is made to determine the barrel end, which has a less taper, than the cutting end, which has a greater taper value, i.e., for the same set of scans. Thus, the needle barrel position can be found. Once the needle barrel end is found, the coordinates for locating the robot gripper parallel to the barrel end of the needle are then calculated at step 395 for transmission to the robot control task as indicated at step 396, in addition to the needle rotational orientation.

Given the barrel end coordinates, the robot gripper device will be able to pick the needle from the conveyor. However, the robot gripper is only able to grip the needle in two orientations: one orientation that is acceptable for direct placement on a conveyor boat, and one orientation that necessitates needle flipping prior to placement on the boat. (FIG. 4(b)). Thus, from the rotational orientation of the needle on the conveyor and the location of the barrel versus tip end, the robot task will know which way the needle will be oriented once gripped by the robot gripper, and know whether to move to the "flip" location.

The Vision Control Task 160 performs error recovery on three types of errors. These errors are grouped as imaging errors, processing errors, and gross errors. The gross errors cause the Task Manager error recovery to respond and stops the Vision Control Task 160 immediately. When an imaging error occurs, the Vision Control Task 160 suspends all execution on the current FOV and requests an early index of the conveyor belt by generating either INDEX CONVEYOR 1 EARLY or INDEX CONVEYOR 2 EARLY signals 231, 233 as discussed above. Receipt of these signals causes no needles to be placed in the parts FIFO and forces both vision/robot systems to pass on the current FOV of needles. If a processing error occurs, the Vision Control Task suspends all processing on the current needle and begins processing a new needle in the same FOV if another needle is available. As a result, the Vision Task does not insert the needle into the parts FIFO.

Conveyor Initiation Task

The Conveyor Initiation Task 190 functions to initiate the Conveyor Indexing Control task 180 and is started whenever the ROBOT ENABLE signal 219 is raised from the PLC 120. Once started, this task requests an INDEX INFEED CONVEYOR 1 (102, 104), signal 237, then waits approximately two (2) seconds, and requests an INDEX INFEED CONVEYOR 2 (102, 104), signal 239, as shown in FIG. 8. The task 1" is then terminated and is not restarted again until the ROBOT ENABLE signal 219 is lowered and raised again.

Task Manager

The Task Manager 240 initializes the software and hardware I/O signals, the global variables, and the vision/robot system tasks. Once the vision/robot system tasks are running, the task manager monitors the integrity and status of each task currently running and the resources that are controlled by these tasks. The status poll signals 247a–247f are indicated in FIG. 8. The resources are the robot, communication ports, and the I/O signal lines. The Task Manager reports any errors to the PLC, via the SYSTEM FAIL signal 222, and the SCADA node, via the SCADA Node Interface Task 195. The SYSTEM FAIL signal 222 is generated whenever a robot (as detected by the Task Manager) has recognized a gross error which prevents it from continuing operation. This signal is active-low and remains low until the Adept robot is reset. Thus, the PLC must lower the ROBOT ENABLE signal 219 immediately upon receiving this signal.

For gross errors occurring with the vision/robot control software, the Task Manager 240 is utilized to detect and recover from these errors by continuously polling the status and integrity of all steady-state tasks and resources during program execution. If it is determined that a gross error has occurred, the SYSTEM FAIL, signal 222 will be raised to the PLC 120 and all tasks except the SCADA Node Interface Task, the Control Panel Task and the Task Manager will be stopped. A code indicating the reason for the last unrecoverable error will be available to the SCADA Node through the SCADA Node Interface Task. In some cases, an error message will be displayed in the Monitor Window of the Adept robot controller. After the SYSTEM FAIL signal is raised, the Task Manager will attempt to correct any problems detected on the robot and notify the operator through the Monitor Window. In most cases, the operator will only need to raise the ROBOT ENABLE signal again to re-set the vision/robot control software.

Control Panel Task

The Control Panel Task 260 presents a mouse controlled panel that allows an operator to access various software "debugging" utilities, to access diagnostics utilities, to control the speed of the robot, and to select new positions that the robot will move to for picking and placing needles. Also, the Control Panel Task allows the operator to stop the vision/robot system tasks from executing.

Figure 14:
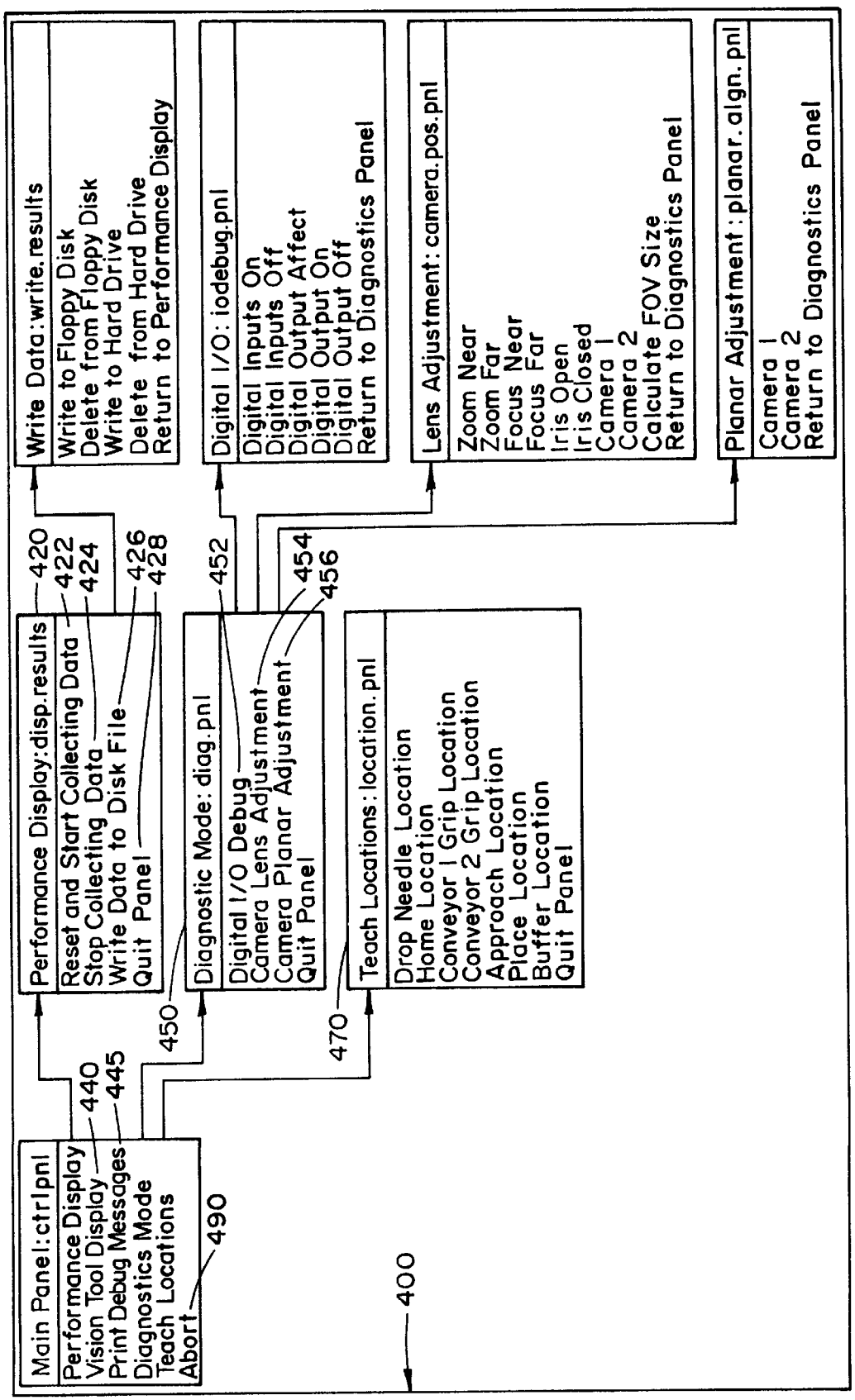
FIG. 14 illustrates the control panel enabling selection of various initialization, diagnostic and debugging operations for the robotic control system.

As shown in FIG. 14, a main "control panel" computer screen 400 is displayed on the operator computer display (not shown) that provides the operator with the following panel button menu choices: a Performance display screen 420; a Vision tool display screen 440; Print debug messages 445; Diagnostics mode 450; a Teach locations mode 470; and an Abort option 490, with details of the Performance display, Diagnostic mode and Teach locations mode screens depicted in the Figure. Each of these menu choices will be described in greater detail hereinbelow.

The Performance display selection 420 implements routines for calculating and displaying various performance and efficiency statistics such as: elapsed run times; needle throughput; number of pictures taken; number of needles inspected; number of needles rejected; number of needles picked; number of objects flushed; number of empty pictures; vision rejects due to timeouts; number of rejects due to needles being too close to edge of FOV; number of rejects due to chord length; number of rejects due to inability to find needle endpoints, e.g., inability to determine barrel end; number of rejects due to being too close to other needles; number of rejects due to out of range of robot; and, the conveyor waiting times. As shown in FIG. 14, the performance display selection provides the option to reset these values to zero and to start collecting data, as depicted as choice 422; to stop collecting data, as depicted as choice 425; to write data to a disk file, as depicted as choice 426; and to quit and close the display, as depicted as choice 428.

The Diagnostics Mode display selection 450 implements routines for enabling an operator to perform the various diagnostics tasks available on the robot controller. For instance, the routines will provide a first choice 452 for performing digital I/O debug, which displays the digital I/O panel to allow the operator to monitor the robot task I/O signals and to affect the output signals. As shown and described herein with respect to FIG. 8, the input signals that may be monitored or affected include: the safe-to-place signal, conveyor 1 settled, conveyor 2 settled, robot enabled, safety interlock, indexed conveyor 1 early, indexed conveyor 2 early, conveyor 1 ready to index, conveyor 2 ready to index and boat conveyor is indexing. The output signals that may be monitored or affected include: robot gripper, index conveyor 1, index conveyor 2, Don't index Camco, needle placed, system failure, needle in gripper, Indexing conveyor 1 early, and Indexing conveyor 2 early.

As shown in FIG. 14, the Diagnostics Mode display selection 450 implements routines 454 for adjusting the camera lens position I/O signals that allows the operator to move a camera lens, e.g., zoom lens, focus, and iris. Such routines will enable an operator to set flags for controlling:

zoom lens distance (near or far); focus (near or far); iris (open or close); the binary vision system for either camera 1,2 or both; and, to calculate and setup a new FOV for the binary vision system. Such field of view set up may include establishing grid coordinates, lines, skew, grid edges, distances between grid edges, setting appropriate vision switches, i.e., parameters for controlling the surrounding light, geometry and Soebel edge filtering, e.g., when implementing binary imaging, etc.

As shown in FIG. 14, the Diagnostics Mode display selection 450 additionally implements routines 454 for determining whether the current camera alignment is acceptable. If the alignment is not acceptable, the program will instruct the operator how to adjust the camera mount of each camera. Such routines enable the operator to: set up camera parameters such as max area, min area, max hole area, min hole area; set up communication paths with each of the cameras; setup the system parameters gain, offset, and threshold for adjusting the iris as needed for the specified camera; run a focusing algorithm for bringing the camera in focus; and, align the grid lines. The focusing algorithm includes the steps of: taking the camera out of focus; taking a picture to determine if the grid is present, obtaining the pixel area that the grid possesses at that focus; looping through steps for bringing the camera into focus, i.e. obtaining the maximum pixel area of the grid image which is in focus; and, once the camera is in focus, setting the edge strength.

As shown in FIG. 14, the Teach locations Mode display selection 470 implements routines for displaying the teach locations panel enabling an operator to teach and set parameters for new locations including: the drop needle location 472; the robot home location 474; conveyor 1 grip location 476; the conveyor 2 grip location 478; the approach location 480; the place location 482; and, the buffer locations 484.

SCADA Node Interface Task

The Supervisor Control and Data Acquisition ("SCADA") Node Interface task 195 polls the SCADA Node RS-232 interface for messages from the SCADA node and the control computer 46. The task will act as slave to SCADA Node requests for Adept and camera set-up procedures necessitated by product changeovers. These requests are valid only when the ROBOT ENABLE signal 219 is deactivated. Preferably, during calibration, needle parameters and types will be read from the SCADA node 195 and will know which needle types require a correct orientation for pickup. If one of these types is determined to be in the incorrect orientation, the robot will flip the needle in the manner described.

Lens Control Task

The Lens Control Task 270 is initiated only when the SCADA node requests a new product to be introduced to the vision system and is executed only as an off-line process. The Lens Control Task 270 accepts the new needle parameters and adjusts the field-of-view size for both cameras to accommodate the new product size. The zoom, focus, and iris lenses are affected by this new product introduction, as well as internal vision system parameters, such as gain, binary threshold, and offset, used for imaging. Once the cameras are adjusted, the task is suspended until another new product is introduced to the vision/robot system.

Product Changeover

Prior to enabling the robots to begin the needle infeed process, a Needle Changeover procedure is invoked to inform the Vision and Robot Control tasks of the control system software of the type and size of the needles to be processed. This needle changeover procedure must be completed before making needle batch changes. If a changeover is not completed before the first needle batch run after power-up, an error message will be displayed at the FIX/DMACS (SCADA Node) screen when the robots are enabled and the robots will not run. If a changeover is not completed between different needle batch runs, the vision tasks will not identify any needle being run.

Essentially, an operator of the system enters the needle parameters in appropriate units, e.g., millimeters and degrees at the FIX/DMACS screen of the SCADA task 195 through data lines 229. Such needle parameters for use by the Vision tasks include, the needle radius and the radius tolerance, acceptable needle chord angles and their tolerances, and, the needle width and the width tolerance.

In addition to inputting needle change parameters for the vision tasks, initial camera set-up parameters associated with the particular batch of needles to be processed are also input through the SCADA Node for use by the system. As shown in FIG. 8, the software utilizes the information provided by the user via the SCADA Node to automatically adjust the lens for the correct field-of-view size, focus, and zoom parameters prior to enabling the robots.

Precise Positioning

For automatic swaging to take place at the swaging station 200 it is necessary that the needle be precisely oriented within the universal gripper of the rotary swage dial. Thus, the transfer of the needle 39 from the engagement jaws 77,79 of the boat 70 to the gripper device necessarily requires that each needle 39 be in a precisely oriented position. Efficient usage of the robotic arms, gripper, the mechanical finger, and the needle "flip" algorithm containing the improvements described above with respect to FIGS. 9(*a*)–9(*f*) ensures that the robotic assembly 108 loads a needle by its barrel in a conveyor boat in one of two possible orientations.

Figure 11:
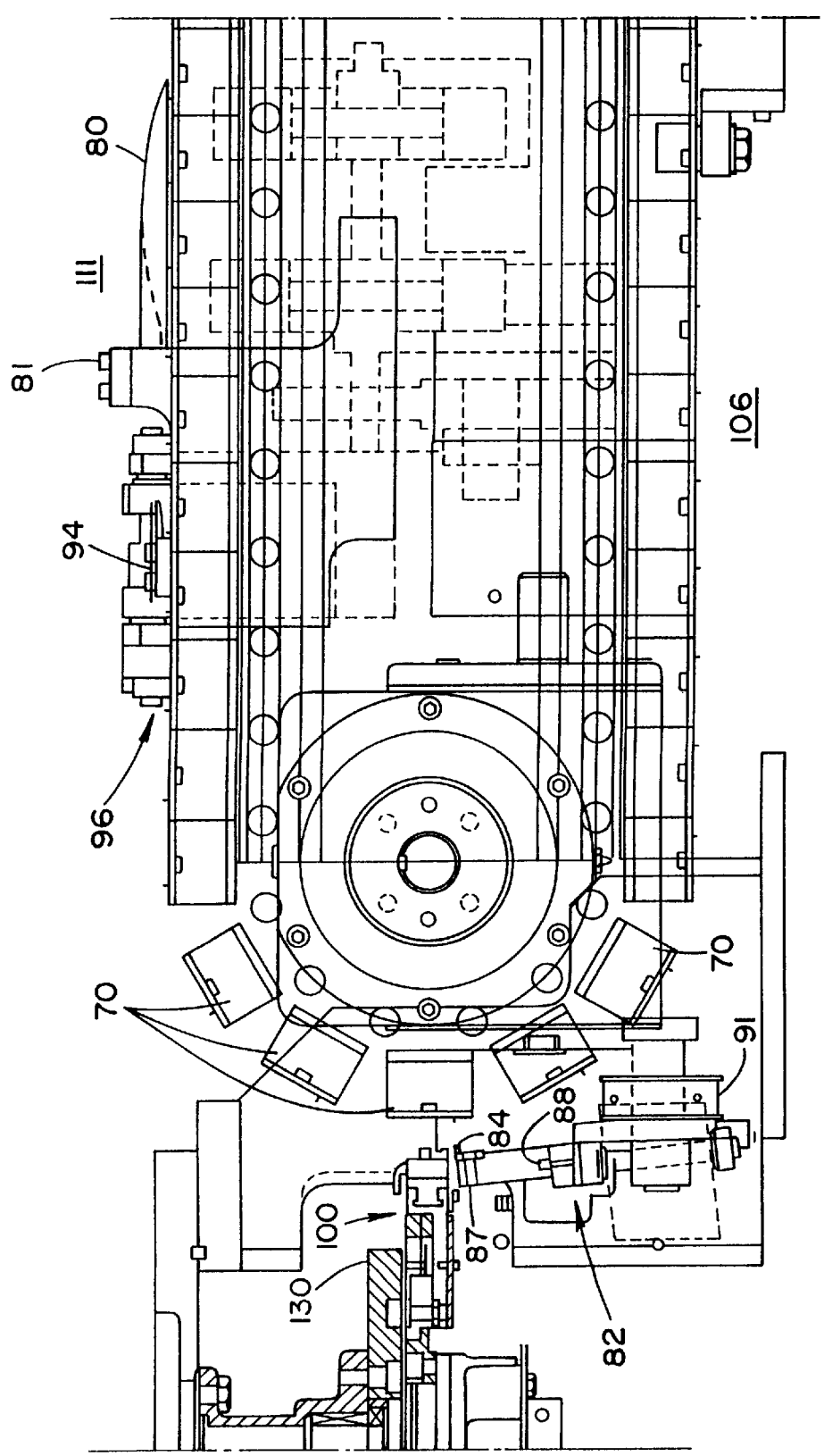
FIG. 11 is a partially cross sectioned elevation view of the precision conveyor of the present invention, illustrating the relative relationships of the precision conveyor, the precision hand off station, the swage dial and the universal gripper used in the present invention.

For other needles besides the cutting-edge super sharp needles 39 that may be fed to the swaging device for automatic swaging, e.g., that may be fed by vibratory bowl needle singulating apparatus such as described in co-pending patent application No. 09/09828, a needle orientation device ("plow") 111 is provided as shown in FIGS. 5 and 11 to orient each needle to a single needle orientation while being conveyed and engaged between jaws 77,79 on conveyor boat 70. The plow comprises an elongated arcuate blade 80 protruding from a mounting bracket 81 as best shown in FIGS. 11. Preferably, as shown in FIG. 5, the plow is mounted at a fixed location along the precision conveyor 106 to enable arcuate blade 80 to scoop needle 39 positioned on the conveyor boat 70 while in forward motion. After contact is made, the arcuate portion of the needle 39 is lifted and rolls over the arcuate blade 80 of the plow 111. Provision of the plow 111 ensures that each needle conveyed to the suture swaging station is oriented in the same direction. The plow device is obviated in the system for orienting supersharp cutting edge surgical needles as orientation of the needle is provided while in the grip of the robot apparatus as described herein.

Figure 11A:
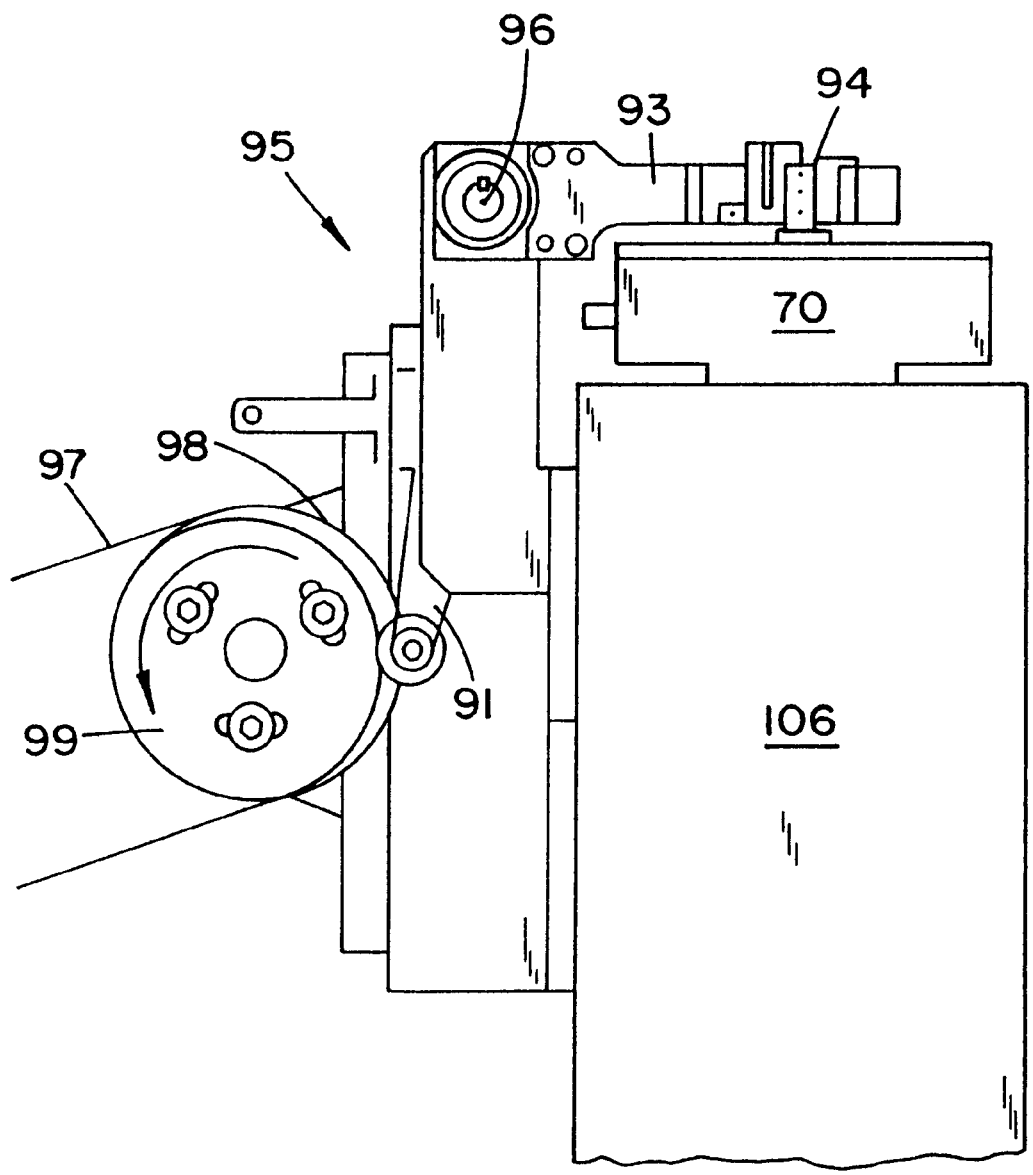
FIG. 11(a) is a diagrammatic elevation view of the pre-positioning stop and the precision conveyor of the present invention.

Another mechanism for further orienting the needle upon the precision conveyor boat is the needle pre-positioning assembly 95 illustrated in FIGS. 11 and 11(*a*). The pre-positioning assembly 95 comprises a pulley 99 driven by an extended drive shaft from Camco drive motor 62 and timing belt 97 for rotating a cam 98 as shown in FIG. 11(a). Cam follower 91 is provided for rotating the pre-positioning assembly about shaft 96, thereby actuating arm stop 93 to reciprocate from a first position above the engagement jaws 77,79 of conveyor boat 70, to a position that enables blade 94 of arm stop 93 to bear upon the barrel end 44 of needle 39 while the precision conveyor boat 70 is conveyed in the forward direction as indicated by the arrow in FIG. 11. Impeding the forward motion of the needle 39 by blade 94 forces the needle to move within engagement jaws 77,79 of the conveyor boat 70 so that the engagement jaws 77,79 engage the needle at a precise-location on its barrel portion. Note that the cam 98, as driven by timing belt 97, is designed so that the arm stop 93 reciprocates in a timed relation with the forward motion of the conveyor boat 70 so that each needle upon each boat 70 is further oriented. After the needle is oriented, the arm stop 93 is reciprocated to its position above the conveyor boat 70 to await the next needle for further orientation.

After the precision conveyor boat 70 is equipped with a needle 39 oriented in the proper direction in the manner described above, it is conveyed to the precision transfer assembly for subsequent transfer to the automatic swaging station 200.

Precise Positioning And The Moveable Hard Stop Assembly

Figure 12A:
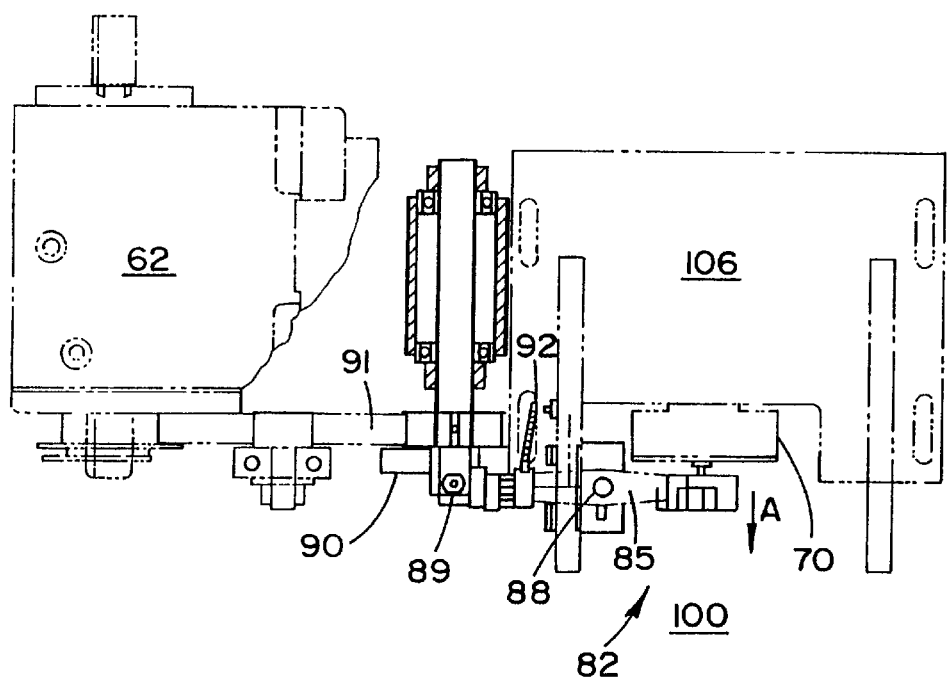
FIG. 12(a) is a partially cross-sectioned plan view of the precision hand off station of the present invention.
Figure 12B:
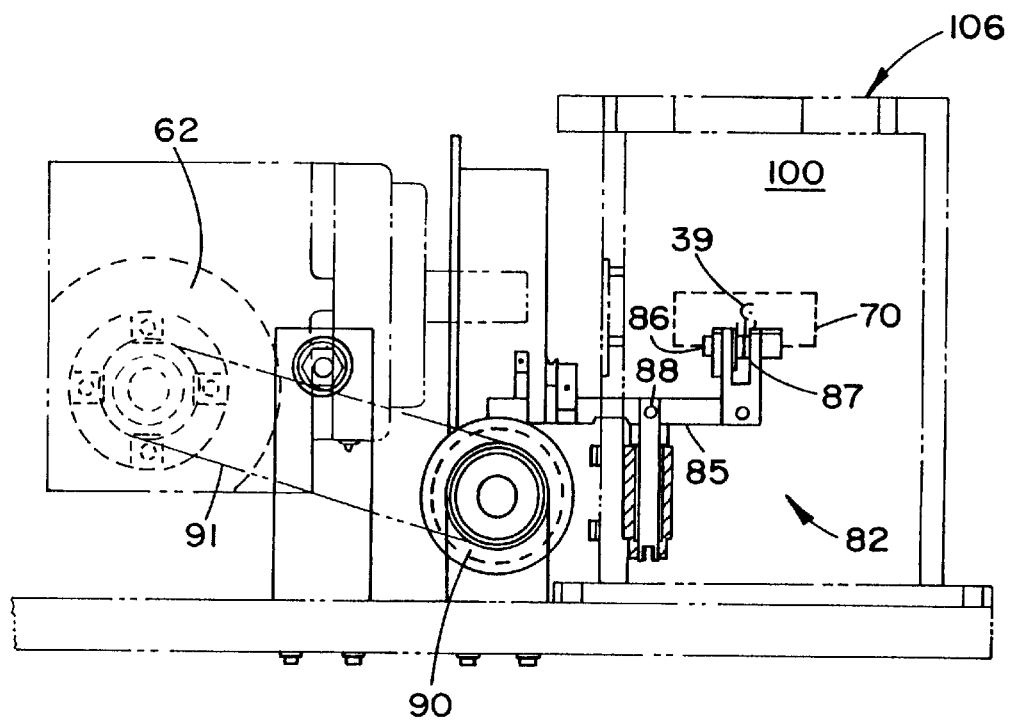
FIG. 12(b) is a partially cross-sectioned elevation view of the precision hand off station illustrated in FIG. 12(a).

After the needle 39 has been pre-positioned as previously described with respect to FIGS. 11 and 11(a), it is conveyed to a precision positioning station 100 for precise placement before hand-off to the automatic swaging system 200. The precise positioning station and a moveable hard stop assembly 82 is illustrated in FIGS. 12(a) and 12(b) where FIG. 12(a) is a top or plan view of the apparatus and FIG. 12(b) is an elevation end view of the apparatus. The hard stop assembly 82 illustrated in FIGS. 12a and 12b is the mechanism used for executing a hard stop of the needle conveyed in conveyor boat 70 when the boat has reached the end of its destination at the hand-off point for the needle swaging station. The hard stop 84 (illustrated in FIGS. 12(a) and 12(b)) provides a precise positioning surface for the needle in boat 70. Typically, the hard stop 84 provides positioning within an accuracy of 0.001 inches of a denoted reference position subsequently used for swaging. The hard stop of the present invention differs from the knife blade stop described with respect to the parent application inasmuch as the knife blade stop in the parent application was a fixed stop mechanism whereas the apparatus illustrated in FIGS. 12(a) and 12(b) is a moveable stop mechanism. The moveable stop assembly 82 is reciprocated out of the way to provide clearance for the conveyor boat 70 as it continues its downward travel to return to the opposite end of the conveyor.

Figure 13A:
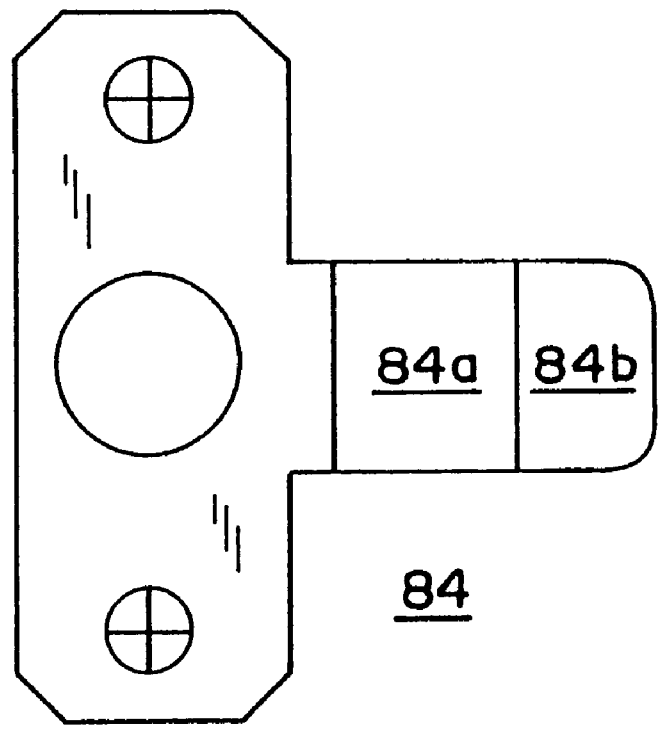
FIG. 13(a) is a plan view of the moveable hard stop used in the precision hand off station of the present invention.
Figure 13B:
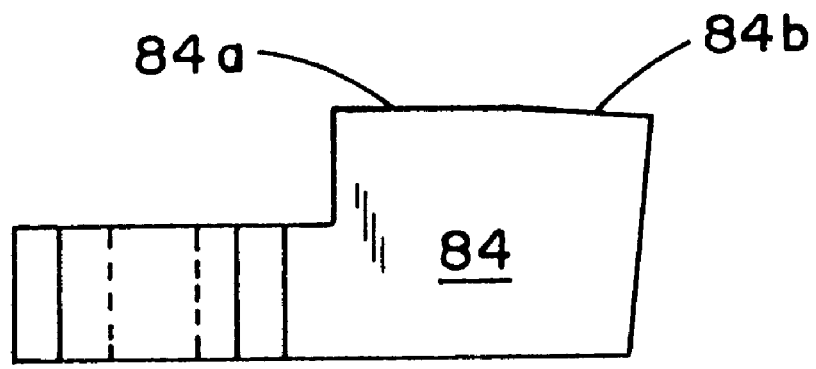
FIG. 13(b) is a side or elevation view of the moveable hard stop illustrated in FIG. 13(a).

As the conveyor boat 70 reaches its final position as illustrated in FIG. 12(a) the moveable hard stop 84 is reciprocated inwardly towards the precision conveyor to receive the butt end of the needle 44 on needle face 84a as illustrated in FIG. 13(a),(b). As the boat 70 arrives at its final location, the gripping jaws of the swage device arrive on the opposite side of the needle hard stop 84. The needle is thus restrained during handoff against downward movement by the needle face 84a of hard stop 84, from side-to-side movement by the jaws 77, 79 of the conveyor boat 70 against rearward motion by the conveyor boat 70 and against forward motion by the face of universal gripper on the swage machine which is to receive the needle. The universal gripper has a pair of jaws which engage the needle to prevent side-to-side motion after transfer is complete. After the jaws 77, 79 are opened and the jaws of the universal gripper are closed, the hard stop 84 is reciprocated in the direction of the arrow A in FIG. 12(a) to provide clearance for movement of jaws 77,79 on boat 70 and for movement of the butt end of the needle as it is moved out of position by the universal gripper. To provide further clearance for the butt end of the needle, and to avoid dislodging it from its precise position, the trailing face of the hard stop 84 is tapered as illustrated at 84b in FIG. 12(b).

The hard stop 84 is spring mounted in a pivot arm 85 by means of a pivot pin 86 and a coil spring 87 which maintains the position of the stop, but provides breakaway capability for the stop in the event of misalignment of the precision conveyor. The breakaway prevents any damage to the conveyor boat 70 from the hard stop 84 in the event of any malfunction of the device. The pivot arm 85 is pivoted about pivot point 88 by means of a guide roller 89 and a face cam 90 which is rotated by an extended drive shaft from the Camco drive motor 62 through belt drive assembly 91. Details regarding the operation of the cam mechanism for providing reciprocal movement of the hard stop mechanism during each dwell period is described in aforementioned U.S. patent application Ser. No. 08/847,133.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed is:

1. A control system for a needle infeed apparatus having first conveyor means with singulated needles positioned randomly thereon for conveyance from a first location toward a second location, said apparatus having one or more robot devices each having a gripper means for picking said needles from said first conveyor means and placing said needles on a precise engagement device, said control system comprising:

(a) control means for pausing said first conveyor means to create a dwell cycle for said infeed apparatus;
 (b) at least one vision tracking means in communication with said control means for generating an image of a selected needle at a predetermined location on said first conveyor means during said dwell cycle and for calculating positional and orientation data for each needle from said generated image;
 (c) memory means for temporarily storing said positional and orientation data received from said vision tracking means; and,
 (d) robot control means for accessing said stored positional and orientation data of a selected said imaged needle and enabling a gripper device of one of said one or more robots to pick up said imaged needle in accordance with its respective positional and orientation data and place said needle in a said precision engagement device, wherein based on said orientation of said needle, said robot control means further enabling said robot gripper means to move to a needle orienting location having a needle orientation device located thereat to enable said needle to contact a needle orientation device and rotate said needle in said gripper means prior to placing said needle in said precision engagement device.

2. The control system for a needle infeed apparatus as claimed in claim 1, wherein said needle infeed apparatus includes a drive means under control of said control means for driving said second conveyor means, said robot control-means generating a first signal for receipt by said control means to enable said drive means to index said conveyor means.

3. The control system for a needle infeed apparatus as claimed in claim 2, wherein said control means generates a first signal for receipt by said vision tracking means indicating that said conveyor means has finished indexing and is in said dwell period.

4. The control system for a needle infeed apparatus as claimed in claim 2, wherein said robot control means automatically polls said memory means to obtain current positional and orientation data of each recognized needle for said one or more robots, said robot control means generating said first signal for receipt by said control means to further index said conveyor means when no positional and orientation data is available in said memory means at a current dwell period.

5. The control system for a needle infeed apparatus as claimed in claim 1, wherein said vision tracking means includes one or more camera means for obtaining a video image of said needles on said conveyor means at said predetermined location within a field-of-view of each of said one or more cameras.

6. The control system for a needle infeed apparatus as claimed in claim 5, wherein each of said cameras has a plurality of vision parameters associated therewith, said vision tracking means including means for comparing needle parameters obtained from said video image with one or more acceptable needle parameters associated with a current batch of needles to be processed, said one or more needle parameters selected from the group including needle radius, needle angle, and needle width.

7. The control system for a needle infeed apparatus as claimed in claim 1, wherein said vision tracking means further includes means for automatically enhancing said image of a needle by recording successive images of said needle and adjusting one or more of a plurality of vision parameters between each successive image until said image of said needle is acceptable for obtaining positional coordinate data therefrom.

8. The control system for a needle infeed apparatus as claimed in claim 7, wherein said vision parameters include field of view size, iris control for said camera and vision system lighting control for said camera.

9. The control system for a needle infeed apparatus as claimed in claim 1, wherein said control means includes means for determining a barrel end and a point end of said needle, said orientation data including data indicating location of said barrel end of said selected needle for downloading to said robot control means.

10. The control system for a needle infeed apparatus as claimed in claim 1, wherein said means for determining a barrel end includes means for determining an amount of taper at each end of said needle, said barrel end being an end with less taper than said other end.

11. The control system for a needle infeed apparatus as claimed in claim 10, wherein said precise engagement device is located on a second conveyor means having a drive means associated therewith for indexing said needle to said processing location, said robot control means generating a signal for receipt by said control means requesting said control means to pause said indexing of said second conveyor means to create a second dwell period.

12. The control system for a needle infeed apparatus as claimed in claim 11, wherein said control means generates a signal for receipt by said robot control means indicating that said robot gripper means may place said needle in said engagement apparatus during said second dwell period.

13. The control system for a needle infeed apparatus as claimed in claim 11, wherein said robot control means generates a signal for receipt by said control means indicating that said one or more robots have placed said needles in said engagement apparatus, said control means enabling first and second jaws of said engagement apparatus to grip said needles placed therein.

14. A method for controlling an automatic infeed apparatus for feeding surgical needles from one location to another location, said infeed apparatus having a first conveyor having randomly positioned needles located thereon, a second conveyor having a plurality of precision needle engagement devices located thereon, and one or more robot means each having a gripper means for picking up a needle from said indexing conveyor, said method comprising the steps of:

(a) pausing said first conveyor to create a dwell time for said infeed apparatus;

(b) imaging said needles on said first conveyor with a vision tracking means during said dwell time to create an image of said needles;

(c) calculating positional and orientation data from said image of a selected needle and determining a barrel end and a point end for said selected needle;

(d) locating said gripper means at said barrel end of said needle;

(e) determining a location of said needle point end with respect to said located gripper means;

(f) picking up said selected needle from said first conveyor;

(g) moving said gripper means gripping said needle towards a needle orienting device when a first orientation of said needle point end is determined at step (e);

(h) rotating said needle while gripped by said needle gripper; and, (i) placing each needle in said precision engagement device for subsequent conveyance thereof.

15. The method according to claim 14, wherein step (f) further includes the step of placing each needle in said precision engagement device for subsequent conveyance thereof when a second orientation of said needle point end is determined at step (e).

16. The method for controlling an automatic infeed apparatus for feeding surgical needles from one location to another location according to claim 14, wherein said step (a) of pausing said first conveyor further includes the step of generating a first control signal from said robot means requesting a control means for said first conveyor to inhibit motion thereof during said dwell time.

17. The method according to claim 16, wherein said processing step (c) further includes the steps of:

determining one or more needle parameter values for needles identified in said image, said one or more needle parameters selected from the group including needle radius, needle angle, and needle width; and comparing each of said needle parameters values obtained from said image with a predetermined range of acceptable needle parameter values associated with a current batch of needles being processed.

18. The method according to claim 14, further including the step of generating a second control signal from said robot means for said control means requesting said control means to index said first conveyor means when no acceptable needle locations are available.

19. The method according to claim 14, wherein said step (b) of visually tracking said needles on said conveyor during said dwell time to determine acceptable needle locations for said one or more robot means further comprises the steps of:

generating a signal for said vision tracking means indicating that said first conveyor is in said dwell cycle;

obtaining an image of said needles from one or more camera means each having a field of view at one or more predetermined locations on said conveyor means;

processing said image to determine positional coordinates for recognizable needles present in said image; and, inputting said positional coordinates into a memory means for access by said robot means.

20. The method according to claim 14, wherein said step (i) of placing each said needles in an engagement apparatus further includes the steps of:

pausing said second conveyance having said needle engagement device located thereon to create a second dwell time for said infeed system; and, generating a control signal indicating to said robot gripper means to place a gripped needle in said needle engagement apparatus during said second dwell time.

21. The method according to claim 20, further including the step of generating a signal for enabling a pair of jaws of said engagement apparatus to grip said needle after placement therein by said robot gripper means.

22. The method according to claim 20, further including the step of actuating a push rod means for retracting one jaw of said pair of engagement jaws for enabling the positioning of said needle therebetween, said actuating step occurring prior to the placement of said needle between said pair of engagement jaws.

23. The method according to claim 14, wherein said step (c) of determining a barrel end and a point end for said selected needle, includes the step of determining an amount of taper at each end of said needle, said barrel end being an end with less taper than said other end.

24. A control system for a surgical needle infeed apparatus having first conveyor means with singulated needles positioned randomly thereon for conveyance from a first location toward a second location, said apparatus having one or more robot devices located intermediate said first and second locations, each robot having a gripper means for picking said needles from said first conveyor means and placing said needles on a second conveyor means for conveyance to said second location, said control system comprising:

(a) control means for pausing said first conveyor means to create a dwell cycle for said infeed apparatus;

(b) at least one vision tracking means in communication with said control means for obtaining an image of a selected needle on said first conveyor means during said dwell cycle, said vision tracking means comprising:

i) means for calculating a first set of data representing a location of a barrel end of said surgical needle from said image; and, ii) means for calculating a second set of data representing rotational orientation of said surgical needle on said conveyor from said image;

(c) means for inputting said first and second sets of data to said robot device; and, (d) means for enabling said gripper device of one of said one or more robots to pick up said imaged needle in accordance with said first and second sets of data and place said needle directly in said second conveyor means when a first condition is satisfied, and further enabling said gripper device to move to a third location to enable said needle to rotate said needle in said gripper means prior to placing said needle on said second conveyor means when a second condition is satisfied.

25. The control system for a surgical needle infeed apparatus as claimed in claim 24, wherein said first condition is satisfied when said needle is rotationally oriented on said first conveyor in a manner advantageous for said robot device to pick and directly place said needle on to said second conveyor at a first orientation.

26. The control system for a surgical needle infeed apparatus as claimed in claim 25, wherein said second condition is satisfied when said needle is rotationally oriented on said first conveyor in a manner that would enable said robot device to pick and directly place said needle on to said second conveyor in a second orientation.

27. The control system for a surgical needle infeed apparatus as claimed in claim 24, further including a drive means for controlling movement of said first and second conveyor means, said robot device instructing said drive means to pause said first conveyor during said dwell period to enable gripping of said needle thereon, and further enabling said drive means to pause said second conveyor for a dwell period to enable direct needle placement thereon.

28. The control system for a surgical needle infeed apparatus as claimed in claim 24, wherein said needle includes first and second endpoints, said means for calculating said first set of data includes:

means for determining the location of first and second endpoints of said needle;

determining an amount of taper of each said needle endpoint;

comparing said amount of taper determined for each said needle endpoint, and;

determining a barrel end for said needle based on said comparison.

29. The control system for a surgical needle infeed apparatus as claimed in claim 28, wherein said barrel end is determined to be an endpoint having the smallest amount of taper.

30. The control system for a surgical needle infeed apparatus as claimed in claim 24, wherein said vision tracking means includes a vision camera having positional coordinates defined in a field of view, said means for calculating said second set of data includes:

means for determining location of both endpoints in said vision camera's field of view and locations of needle edges;

means for calculating a predetermined location associated with said needle;

means for computing a first line capable of intersecting a said endpoint and said predetermined location;

means for computing a second line of predetermined length and predetermined direction from said first line;

means for determining whether said second line intersects a needle edge, wherein said rotational orientation is determined according to whether said second line intersects a needle edge; said location of said predetermined.

31. The control system for a surgical needle infeed apparatus as claimed in claim 30, wherein said surgical needle has a plurality of needle parameters associated therewith, said needle parameters including needle radius, needle angle, and needle width.

32. The control system for a surgical needle infeed apparatus as claimed in claim 31, wherein said predetermined length of said second line is determined in accordance with said needle parameters.

* * * * *